(12) United States Patent
Dhar et al.

(10) Patent No.: US 7,994,190 B2
(45) Date of Patent: Aug. 9, 2011

(54) MODULATORS OF GLUCOCORTICOID RECEPTOR, AP-1, AND/OR NF-κB ACTIVITY AND USE THEREOF

(75) Inventors: T. G. Murali Dhar, Newtown, PA (US); Hai-Yun Xiao, Belle Mead, NJ (US); James E. Sheppeck, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 137 days.

(21) Appl. No.: 12/513,228

(22) PCT Filed: Oct. 31, 2007

(86) PCT No.: PCT/US2007/083083
§ 371 (c)(1),
(2), (4) Date: Jul. 30, 2009

(87) PCT Pub. No.: WO2008/057855
PCT Pub. Date: May 15, 2008

(65) Prior Publication Data
US 2010/0190820 A1    Jul. 29, 2010

Related U.S. Application Data

(60) Provisional application No. 60/855,864, filed on Nov. 1, 2006.

(51) Int. Cl.
*A61K 31/437* (2006.01)
*C07D 401/02* (2006.01)
(52) U.S. Cl. ...................... 514/300; 546/121
(58) Field of Classification Search .............. 514/300; 546/121
See application file for complete search history.

(56) References Cited

U.S. PATENT DOCUMENTS

| | | | |
|---|---|---|---|
| 2004/0235888 A1* | 11/2004 | Yamamori et al. | 514/309 |
| 2004/0266751 A1 | 12/2004 | King | |
| 2005/0234058 A1 | 10/2005 | Mahaney et al. | |
| 2007/0037974 A1 | 2/2007 | Brotherton-Pleiss et al. | |

FOREIGN PATENT DOCUMENTS

| | | |
|---|---|---|
| EP | 0 644 182 | 3/1995 |
| WO | WO 92/19239 | 11/1992 |
| WO | WO 00/17201 | 3/2000 |
| WO | WO 03/024962 | 3/2003 |
| WO | WO 2004/080390 | 9/2004 |
| WO | WO 2004/108137 | 12/2004 |
| WO | WO 2005/037279 | 4/2005 |
| WO | WO 2005/037283 | 4/2005 |
| WO | WO 2006/071609 | 7/2006 |
| WO | WO 2006/132275 | 12/2006 |
| WO | WO 2008/057856 | 5/2008 |
| WO | WO 2008/057857 | 5/2008 |
| WO | WO 2008/057859 | 5/2008 |
| WO | WO 2008/057862 | 5/2008 |

OTHER PUBLICATIONS

Baldwin, Jr., A.S., "The transcription factor NF-κB and human disease", The Journal of Clinical Investigation, vol. 107, No. 1, pp. 3-6 (2001).
Burke, J.R., "Targeting IκB kinase for the treatment of inflammatory and other disorders", Current Opinion in Drug Discovery & Development, vol. 6, No. 5, pp. 720-728 (2003).
Caldenhoven, E. et al., "Negative Cross-Talk between ReIA and the Glucocorticoid Receptor: A Possible Mechanism for the Antiinflammatory Action of Glucocorticoids", Molecular Endocrinology, vol. 9, No. 4, pp. 401-412 (1995).
Chakravarti, D. et al., "Role of CBP/P300 in nuclear receptor signalling", Nature, vol. 383, pp. 99-103 (1996).
Diamond, M.I. et al., "Transcription Factor Interactions: Selectors of Positive or Negative Regulation from a Single DNA Element", Science, vol. 249, pp. 1266-1272 (1990).
Firestein, G.S. et al., "Signal Transduction and Transcription Factors in Rheumatic Disease", Arthritis & Rheumatism, vol. 42, No. 4, pp. 609-621 (1999).
Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

(Continued)

*Primary Examiner* — Susannah Chung
(74) *Attorney, Agent, or Firm* — Laurelee A. Duncan; Burton Rodney

(57) ABSTRACT

Novel non-steroidal compounds are provided which are useful in treating diseases associated with modulation of the glucocorticoid receptor, and/or AP-1 and/or NF-κB activity including inflammatory and immune diseases, obesity and diabetes having the structure of formula (I):, its enantiomers, diastereomers, or a pharmaceutically-acceptable salt, or hydrate, thereof, wherein the group X is O or $(R^x)(R^y)$; is heterocyclo or heteroaryl; E is —N—, —$NR_1$—, —O—, —C(=O), —S—, —$SO_2$—, or —$CR_2$—; F is —N—, —$NR_{1a}$, —O—, —C(=O), —S—, —$SO_2$—, or —$CR_{2a}$—; G is independently N, —$NR_{1b}$—, —O—, —C(=O), —S—, —$SO_2$— or —$CR_{2b}$— provided that the heterocyclic ring formed does not contain a S—S or S—O bond and at least one of E, F and G is a hetero atom; and Ma, $R^x$, $R^y$, $R_1$, $R_{1a}$, $R_{1b}$, $R_2$, $R_{2a}$, $R_{2b}$, $R_4$, $R_{5a}$, $R_6$, $R_7$, X, $Z_a$ and Z are as defined herein. Also provided are pharmaceutical compositions and methods of treating inflammatory- or immune-associated diseases employing said compounds.

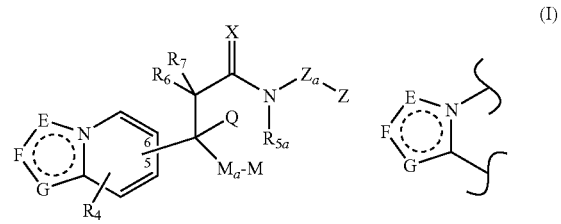

(I)

14 Claims, No Drawings

OTHER PUBLICATIONS

Kamei, Y. et al., "A CBP Integrator Complex Mediates Transcriptional Activation and AP-1 Inhibition by Nuclear Receptors", Cell, vol. 85, pp. 403-414 (1996).

Manning, A.M., et al., "Targeting JNK for Therapeutic Benefit: from Junk to Gold?", Nature, vol. 2, pp. 554-565 (2003).

Miesfeld, R. et al., "Characterization of a steroid hormone receptor gene and mRNA in wild-type and mutant cells", Nature, vol. 312, pp. 779-781 (1984).

Peltz, G., "Transcription factors in immune-mediated disease", Current Opinion in Biotechnology, vol. 8, pp. 467-473 (1997).

Reichardt, H.M. et al., "DNA Binding of the Glucocorticoid Receptor is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v-erb-A oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

Yin, L. et al., "New Calcineurin Inhibiting 3-Dimethylaminopropyl Substituted Diarylheterocycles by Sonogashira Reactions and Catalytic Hydrogenation", J. Heterocyclic Chem., vol. 42, pp. 1369-1379 (2005).

* cited by examiner

MODULATORS OF GLUCOCORTICOID RECEPTOR, AP-1, AND/OR NF-κB ACTIVITY AND USE THEREOF

FIELD OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation,* 107:3 (2001); Firestein, G. S. and Manning, A. M., *Arthritis and Rheumatism,* 42:609 (1999); and Peltz, G., *Curr. Opin. in Biotech.,* 8:467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.,* 2:554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.,* 6(5):720-728 (September 2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science,* 228:740-742 (1985); Weinberger et al., *Nature,* 318:670-672 (1985) and for results in rats see Miesfeld, R., *Nature,* 312:779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell,* 62:1189 (1990); Yang-Yen, H. F. et al., *Cell,* 62:1205 (1990); Diamond, M. I. et al., *Science,* 249:1266 (1990); and Caldenhoven, E. et al., *Mol. Endocrinol.,* 9:401 (1995). Other mechanisms such as sequestration of co-activators by GR have also been proposed. See Kamei, Y. et al., *Cell,* 85:403 (1996); and Chakravarti, D. et al., *Nature,* 383:99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell,* 93:531 (1998) and Reichardt, H. M., *EMBO J.,* 20:7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents. However their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and/or obesity and diabetes, and to a method for using such compounds to treat these and related diseases.

In accordance with one aspect of the invention, compounds are provided having the structure of formula I

I its enantiomers, diastereomers, tautomers, a prodrug ester thereof, or a pharmaceutically-acceptable salt, or hydrate, thereof, wherein the side chain group is attached to the benzo ring at the 5- or 6-position;

is heterocyclo or heteroaryl;
  E is selected from —N—, —NR$_1$—, —O—, —C(=O)—, —S—, —SO$_2$—, and —CR$_2$—;
  F is selected from —N—, NR$_{1a}$, —O—, —C(=O)—, —S—, —SO$_2$—, and —CR$_{2a}$—;
  G is selected from N, —NR$_{1b}$—, —O—, —C(=O)—, —S—, —SO$_2$—, and —CR$_{2b}$—,
provided that the heterocyclic ring formed does not contain a S—S or S—O bond;
  X is selected from O and (R$^x$)(R$^y$);
  M is selected from hydrogen, alkyl, alkenyl, alkynyl, cycloalkyl, cycloalkenyl, aryl, heterocyclo, and heteroaryl;
  M$_a$ is a linker between C and M and is selected from a bond; C$_1$-C$_5$ alkylene; C$_1$-C$_5$ alkylene which includes at any position in the chain a) a nitrogen which is substituted with alkyl, b) an oxygen, c) a sulfur, or d) an SO$_2$ group; —C(R$_{m^1}$)(R$_{m^2}$)C(=O)N(R$_{m^3}$)—; —C(=O)N(R$_{m^1}$)C(R$_{m^2}$)(R$_{m^3}$)—; —N(R$_{m^3}$)C(=O)C(R$_{m^1}$)(R$_{m^2}$)—; —C(R$_{m^1}$)(R$_{m^2}$)S(=O)$_2$N(R$_{m^3}$)—; —S(=O)$_2$N(R$_{m^1}$)C(R$_{m^2}$)(R$_{m^3}$)—; and —N(R$_{m^1}$)C(=O)N(R$_{m^2}$)—; where R$_{m^1}$, R$_{m^2}$ and R$_{m^3}$ are the same or different and at each occurrence independently selected from H and C$_1$-C$_4$ alkyl, or R$_{m^1}$ and R$_{m^2}$ combine to form a C$_{3-6}$ carbocyclic or heterocyclo ring;
  Q is selected from
    (i) hydrogen, halogen, nitro, cyano, hydroxy, unsubstituted C$_1$-C$_4$ alkyl, and substituted C$_1$-C$_4$ alkyl; or
    (ii) Q and R$_6$ are combined with the carbons to which they are attached to form a 3- to 6-membered cycloalkyl or cycloheteroalkyl (or heterocyclo) ring; or
    (iii) Q and M-M$_a$ are combined with the carbon to which they are attached to form a 3-7 membered ring optionally containing 0, 1 or 2 heteroatoms which are the same or different and are independently selected form the group consisting of O, S, SO, SO$_2$, and N—R$_{5b}$, provided that the heterocyclic ring formed does not contain a S—S or S—O bond, wherein this ring may be optionally substituted with 0, 1 or 2 R$_3$ groups or carbonyl;
  when X is O, Z is selected from
    (i) alkyl, cycloalkyl, heterocyclo, alkylsulfonyl, aryl, and heteroaryl; or
    (ii) Z is combined with R$_{5a}$ and to the carbon to which they are attached to form a 3-6 membered heterocyclic ring which is optionally substituted with 1-2 R$_3$ groups or carbonyl;
  or when X=(R$^x$)(R$^y$), Z is selected from
    (i) alkyl, cycloalkyl, heterocyclo, aryl, heteroaryl, —C(=O)NR$_8$R$_9$, —C(=O)R$_8$, —C(NCN)NR$_8$R$_9$, —C(=O)OR$_8$, —SO$_2$R$_8$, and —SO$_2$NR$_8$R$_9$; or
    (ii) Z is combined with R$_{5a}$ to form a 3-6 membered heterocyclic ring which is optionally substituted with 1-2 R$_3$ groups or carbonyl;
  Z$_a$ is a linker between N and Z and is selected from a bond; C$_{1-5}$ alkylene; C$_{1-5}$ alkylene which includes at any position in the chain a) a nitrogen which is substituted with alkyl, b) an oxygen, c) a sulfur, or d) an SO$_2$ group; —C(R$_{z^1}$)(R$_{z^2}$)C(=O)N(R$_{z^3}$)—; —C(=O)N(R$_{z^1}$)C(R$_{z^2}$)(R$_{z^3}$)—; —C(R$_{z^1}$)(R$_{z^2}$)S(=O)$_2$N(R$_{z^3}$)—; and —S(=O)$_2$N(R$_{z^1}$)C(R$_{z^2}$)(R$_{z^3}$)—; where R$_{z^1}$, R$_{z^2}$ and R$_{z^3}$ at each occurrence are independently selected from H and C$_1$-C$_4$ alkyl;
  R$_1$, R$_{1a}$, R$_{1b}$, R$^x$ and R$^y$ are the same or different and at each occurrence are independently selected from hydrogen, alkyl, alkenyl, alkynyl, cycloalkyl, cycloalkenyl, aryl, heteroaryl, and heterocyclo;
  R$_2$, R$_{2a}$ and R$_{2b}$ are the same or different and at each occurrence are independently selected from hydrogen, halogen, alkyl, alkenyl, alkynyl, nitro, cyano, —OR$_{10}$, NR$_{10}$R$_{11}$, —C(=O)R$_{10}$, CO$_2$R$_{10}$, —C(=O)NR$_{10}$R$_{11}$, —O—C(=O)R$_{10}$, —NR$_{10}$C(=O)R$_{11}$, —NR$_{10}$C(O)OR$_{11}$, —NR$_{10}$C(S)OR$_{11}$, —S(O)$_p$R$_{12}$, —NR$_{10}$SO$_2$R$_{12}$, —SO$_2$NR$_{10}$R$_{11}$, cycloalkyl, cycloalkenyl, cycloalkynyl, heterocyclo, aryl, and heteroaryl;
  R$_3$ is independently at each occurrence selected from hydrogen, halogen, alkyl, alkenyl, alkynyl, cyano, —OR$_{13}$, —NR$_{13}$R$_{14}$, —C(=O)R$_{13}$, —CO$_2$R$_{13}$, —C(=O)NR$_{13}$R$_{14}$, —O—C(=O)R$_{13}$, —NR$_{13}$C(=O)R$_{14}$, —NR$_{13}$C(O)OR$_{14}$, —NR$_{13}$C(S)OR$_{14}$, —S(O)$_p$R$_{15}$, —NR$_{13}$SO$_2$R$_{15}$, —SO$_2$NR$_{13}$R$_{14}$, cycloalkyl, cycloalkenyl, cycloalkynyl, heterocyclo, aryl, and heteroaryl;
  R$_4$ is selected from hydrogen, halogen, alkyl, alkenyl, alkynyl, cyano, and C$_1$-C$_4$ alkoxy;
  R$_{5a}$ is selected from hydrogen and alkyl; and
  R$_6$ is selected from hydrogen, halogen, alkyl, alkenyl, alkynyl, nitro, cyano, —OR$_{16}$, —NR$_{16}$R$_{17}$, —C(=O)R$_{17}$, —CO$_2$R$_{17}$, —C(=O)NR$_{16}$R$_{17}$, —O—C(=O)R$_{16}$, —NR$_{16}$C(=O)R$_{17}$, —NR$_{16}$C(=O)OR$_{17}$, —NR$_{16}$C(=S)OR$_{17}$, —S(O)$_p$R$_{15}$, —NR$_{16}$SO$_2$R$_{15}$, —SO$_2$NR$_{16}$R$_{17}$, cycloalkyl, cycloalkenyl, heterocyclo, aryl, and heteroaryl;
  R$_7$ is selected from hydrogen, halogen, alkyl, haloalkyl, alkenyl, alkynyl, nitro, cyano, —OR$_{19}$, —NR$_{19}$R$_{20}$, —C(=O)R$_{19}$, —CO$_2$R$_{19}$, —C(=O)NR$_{19}$R$_{20}$, —O—C(=O)R$_{19}$, —NR$_{19}$C(=O)R$_{20}$, —NR$_{19}$C(=O)OR$_{20}$, —NR$_{19}$C(=S)OR$_{20}$, —S(O)$_p$R$_{21}$, —NR$_{19}$SO$_2$R$_{21}$, —SO$_2$NR$_{19}$R$_{20}$, cycloalkyl, cycloalkenyl, cycloalkynyl, heterocyclo, aryl, and heteroaryl;
  or R$_6$ and R$_7$ are taken together with the carbon to which they are attached to form a cycloalkyl, cycloalkenyl, or heterocyclo ring;

$R_{5b}, R_8, R_9, R_{10}, R_{11}, R_{13}, R_{13a}, R_{14}, R_{16}, R_{17}, R_{19}$ and $R_{20}$ are the same or different and at each occurrence are independently selected from
(i) hydrogen, alkyl, alkenyl, alkynyl, cycloalkyl, cycloalkenyl, aryl, heteroaryl, and heterocyclo; or
(ii) with respect to Z, $R_8$ taken together with $R_9$, and/or with respect to $R_3$ and $R_6$, $R_{15}$ is taken together with $R_{16}$, and/or with respect to $R_6$ and $R_7$, $R_{18}$ is taken together with $R_{19}$, and/or with respect to $R_7$, $R_{20}$ is taken together with $R_{21}$ to form a 4- to 6-membered heteroaryl or heterocyclo ring;

$R_{12}, R_{15}, R_{18}$ and $R_{21}$ are the same or different and are independently selected from alkyl, alkenyl, alkynyl, cycloalkyl, cycloalkenyl, aryl, heteroaryl, and heterocyclo; and p is 0, 1 or 2,
provided that where the ring system

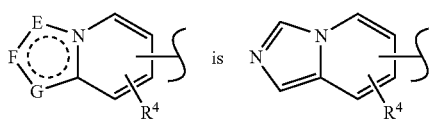

and Q and $M_a$-M are independently H, $CH_3$ or $C_2H_5$, then $Z_a$—Z is other than

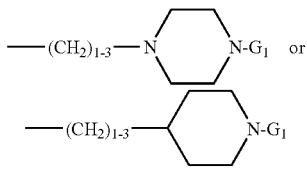

where $G_1$ is a heteroaryl, acetyl, carbamoyl, or —C(=S)CH$_3$ or —C(=S)C$_2$H$_5$.

In the ring system

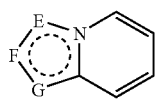

employed in the compounds of formula I, it is preferred that
E is $CR_2$;
F is N or $CR_{2a}$;
and G is N or $CR_{2b}$.
More preferred are the following ring systems:

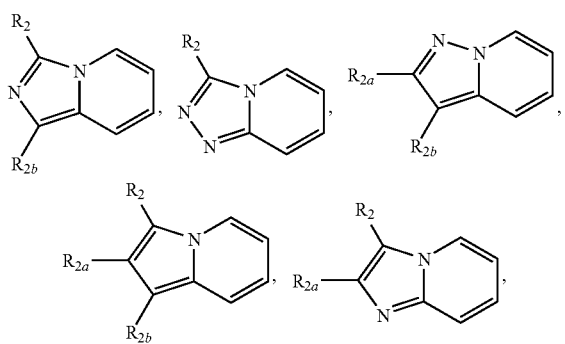

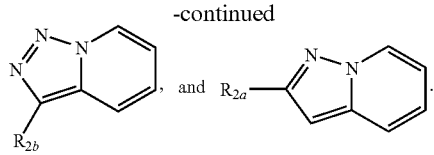

It is preferred that in the compounds of formula I,

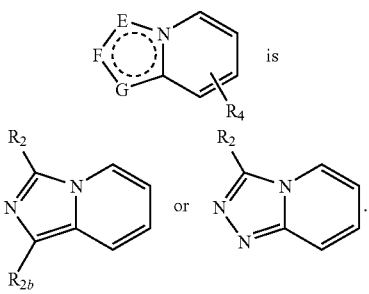

In more preferred embodiments of compounds of formula I

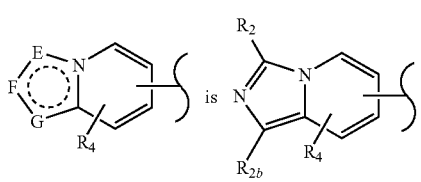

a)

where $R_2$ is aryl or H,
$R_{2b}$ is H, halogen, aryl or heteroaryl,
and $R_4$ is H or methyl; or

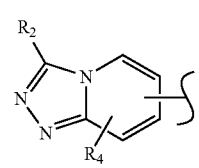

b)

where $R_2$ is selected from H, aryl and alkyl; and $R_4$ is H or methyl;
X is $(R^x)(R^y)$ where $R^x$ and $R^y$ are the same or different and are independently H or alkyl; or
X is O;
M is aryl or H;
$M_a$ is a bond;
Q is H;
$R_{5a}$ is H;
$R_6$ is alkyl or H;
$R_7$ is alkyl or H;
E is $CR_2$ where $R_2$ is H, aryl or alkyl;
F is N;
G is $CR_{2b}$ where $R_{2b}$ is selected from H, halo, substituted aryl such as cyanoaryl, haloaryl, dihaloaryl and hydroxyalkylaryl, and heteroaryl, or
G is N; and
Z is selected from

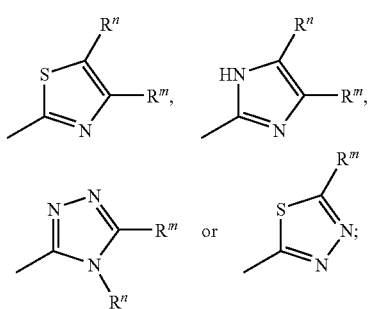

$R^m$ and $R^n$ are the same or different and at each occurrence are independently selected from hydrogen, halogen, cycloalkyl, cyano, —CO$_2$R$^c$, —NR$^a$R$^b$, —C(=O)R$^c$, —C(O)N(R$^a$)(R$^b$), OR % unsubstituted alkyl, substituted alkyl such as haloalkyl and thioalkyl, aryl, heteroaryl, and heterocyclo;

or $R^m$ and $R^n$ combine to form a 5-, 6- or 7-membered carbocyclic, aryl, heteroaryl or cycloheteroalkyl ring which contains 0, 1, 2 or 3 hetero atoms which can be N, O, or S;

$R^a$ and $R^b$ are the same or different and at each occurrence are independently selected from (1) hydrogen, alkyl, C(=O) alkyl, CO$_2$(alkyl), SO$_2$alkyl, alkenyl, alkynyl, amino, substituted amino (NR$^{a^1}$R$^{b^1}$ where R$^{a^1}$ and R$^{b^1}$ are independently selected from H, alkyl or any of the R$^c$ groups as defined below), aryl, heteroaryl, cycloalkenyl, heterocyclo, and cycloalkyl, provided R$^a$ and R$^b$ are not both alkoxy, amino, or substituted amino, or (2) where possible R$^a$ is taken together with R$^b$ to form a heteroaryl or heterocyclo ring;

$R^c$ is selected from hydrogen, alkyl, alkenyl, alkynyl, alkoxy, amino, substituted amino, heteroaryl, heterocyclo, cycloalkyl, and aryl; and $Z_a$ is a bond.

In still more preferred embodiments of compounds of formula I,

X is O, or

X is (R$^x$)(R$^y$), which more preferred is CH$_2$;

R$_6$ is CH$_3$ or H;

R$_7$ is CH$_3$ or H;

M is

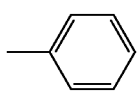

or H;

Q is H;

E is CR$_2$ where R$_2$ is preferably H,

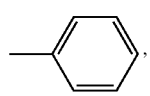

or CH$_3$;

F is N;

G is CR$_{2b}$ where R$_{2b}$ is preferably

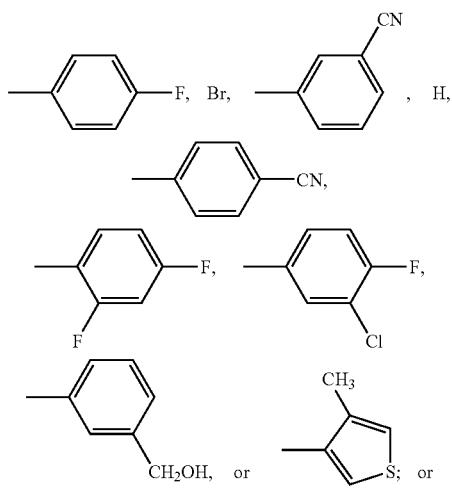

G is N.

In a preferred embodiment, the side chain moiety

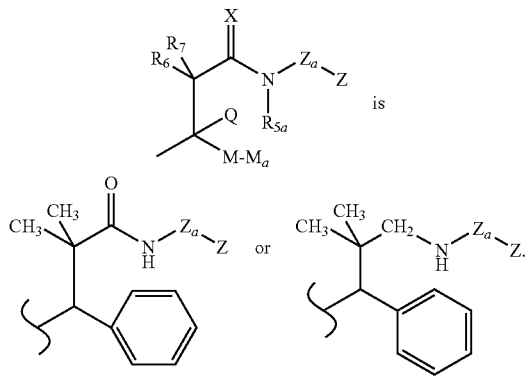

Most preferred are compounds of formula I having the following structure

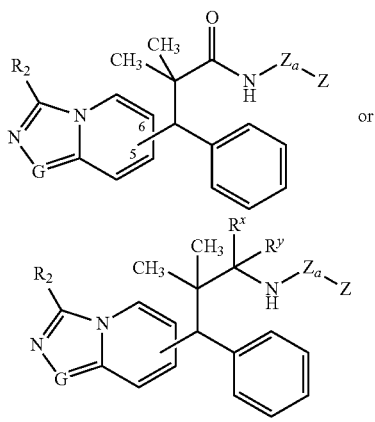

where G is N or CR$_{2b}$;

R$^2$ is H,

or CH<sub>3</sub>;
R<sub>2b</sub> is Br,
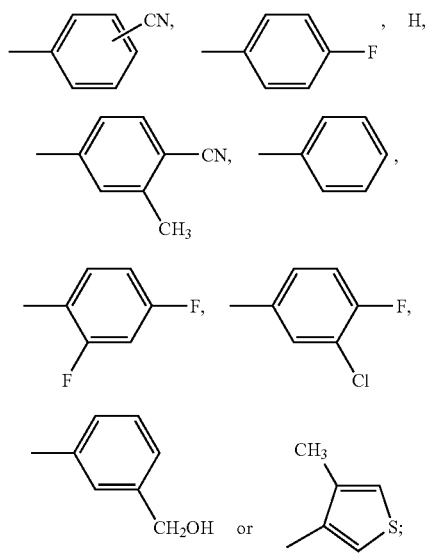
Z is
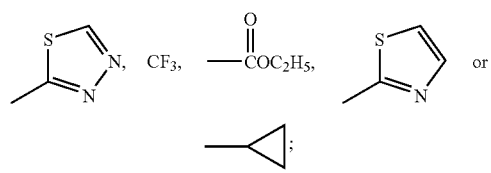
and
Z<sub>a</sub> is a bond, or a pharmaceutically acceptable salt thereof.
The following compounds represent preferred embodiments of compounds of the invention:
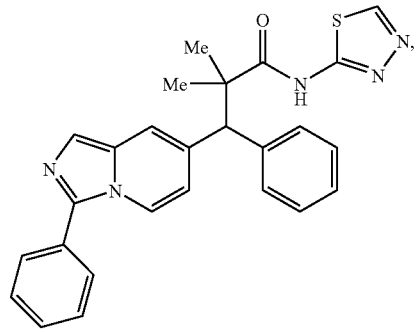
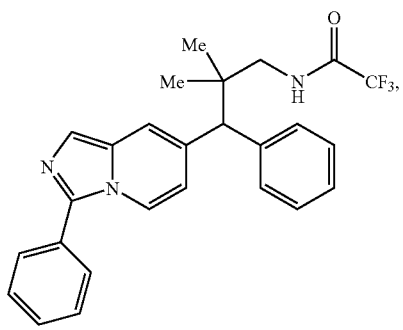
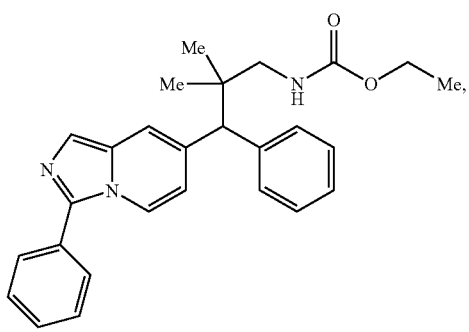
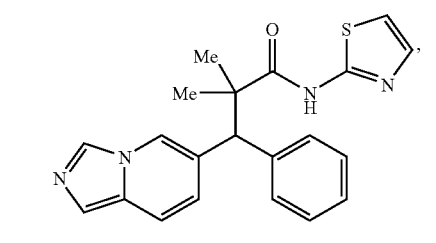
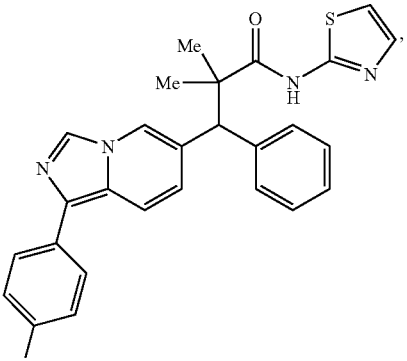
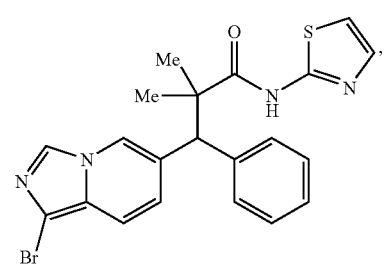

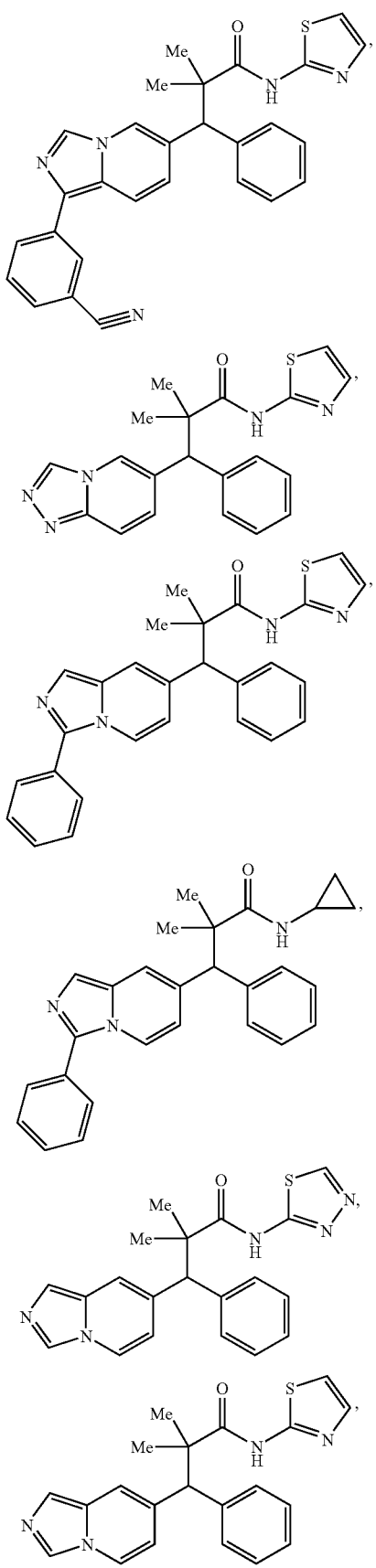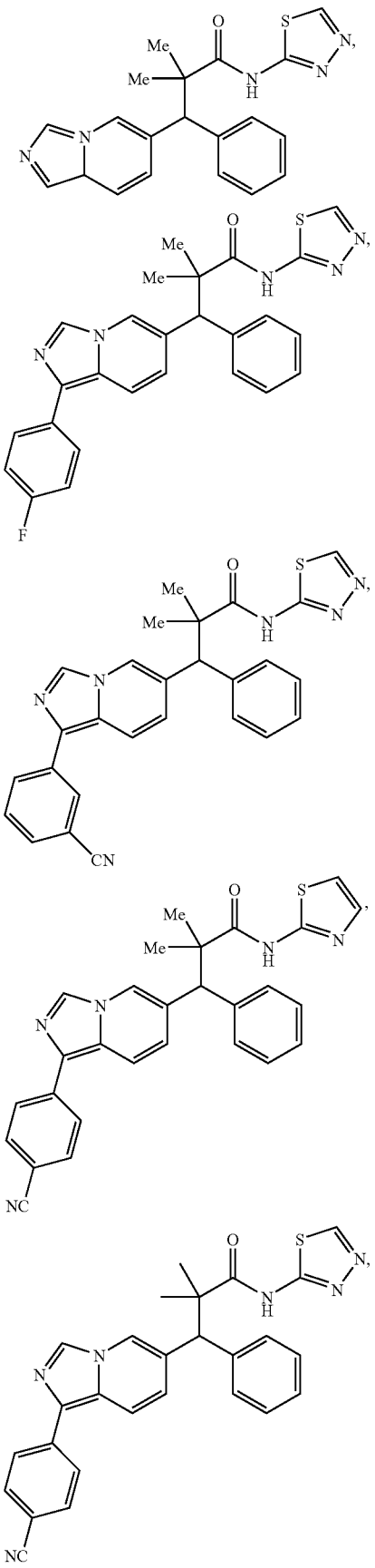

-continued

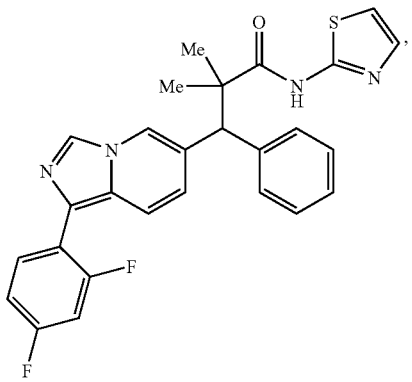

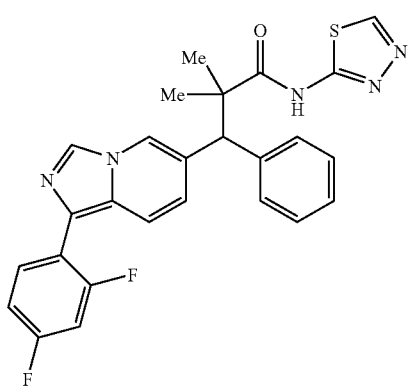

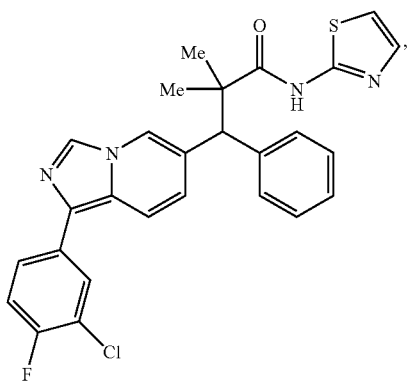

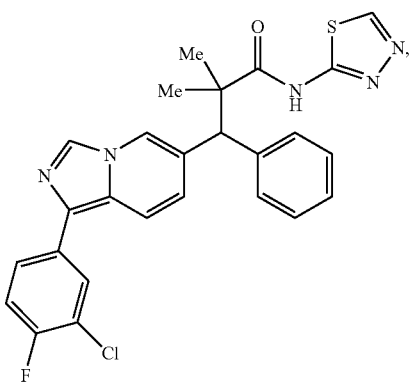

-continued

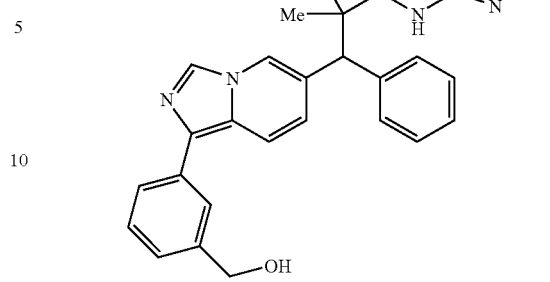

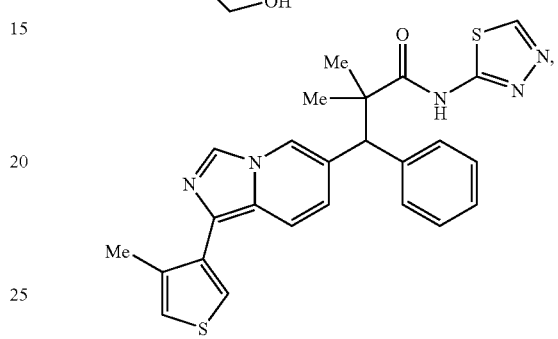

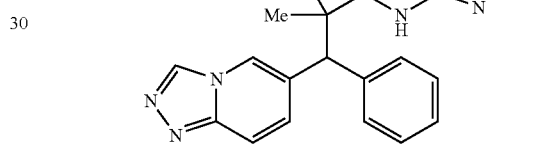

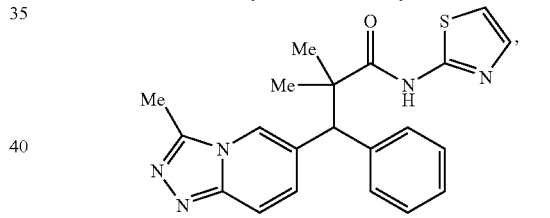

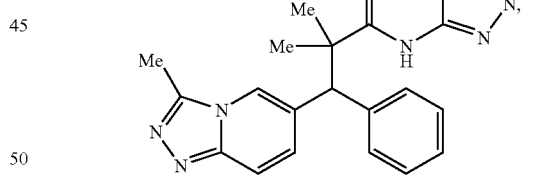

or a pharmaceutically acceptable salt thereof.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, metabolic disease, inflammatory disease, autoimmune disease, and neoplastic disease, as well as other uses as described herein, which including a therapeutically effective amount (depending upon use) of a compound of formula I of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, immune disease, metabolic disease (diabetes and/or obesity), and neoplastic disease. A disease associated with the expression product of a gene whose transcription is stimulated or repressed by glucocorticoid receptors, or a disease associated with AP-1- and/or NF-κB-induced transcription, or a disease associated with AP-1 and/or NF-κB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula I of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κβ (particularly AP-1-) induced transcription, or a method for treating a disease or disorder associated with AP-1 and/or NF-κβ (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes (including Type II diabetes), obesity, glaucoma, muscle loss, facial swelling, personality changes, hypertension, depression, and AIDS, the condition of wound healing, primary or secondary adrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger et al., *Science,* 228:740-742 (1985), and in Weinberger et al., *Nature,* 318:670-672 (1986); rat glucocorticoid receptor as disclosed in Miesfeld, R., *Nature,* 312:779-781 (1985); mouse glucocortoid receptor as disclosed in Danielson, M. et al., *EMBO J.,* 5:2513 (1986); sheep glucocorticoid receptor as disclosed in Yang, K. et al., *J. Mol. Endocrinol.,* 8:173-180 (1992); marmoset glucocortoid receptor as disclosed in Brandon, D. D. et al., *J. Mol. Endocrinol.,* 7:89-96 (1991); and human GR-beta as disclosed in Hollenberg, S. M. et al., *Nature,* 318:635 (1985); Bamberger, C. M. et al., *J. Clin Invest.,* 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" or similar wording is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I diabetes, juvenile diabetes, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhea, pulmonary inflammation, eye uveitis, hepatitis, Graves' disease, Hashimoto's thyroiditis, autoimmune thyroiditis, Behcet's or Sjorgren's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (depigmentation of the skin), alopecia areata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), urticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis.

Accordingly, one embodiment of the present invention is a method of treating a disease or disorder selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, which comprise administering to a patient in need of treatment, a therapeutically effective amount of a compound of formula I.

Metabolic diseases to be treated in accordance with the method of the invention can include Type II diabetes and/or obesity. Type I diabetes and juvenile diabetes may possibly be classified as metabolic diseases to be treated as well.

In a preferred embodiment of the invention, the disease to be treated is an inflammatory or immune associated disease or disorder as defined hereinbefore.

In a preferable embodiment the disease or disorder to be treated is an inflammatory or autoimmune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjorgren's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia areata, autoimmune alopecia, autoimmune hypopituitarism, Guillain-Barre syndrome, and alveolitis; contact hypersensitivity, delayed-type hypersensitivity, contact dermatitis, urticaria, skin allergies, respiratory allergies, hayfever, gluten-sensitive enteropathy, osteoarthritis, acute pancreatis, chronic pancreatitis, acute respiratory distress syndrome, Sezary's syndrome, restenosis, stenosis and atherosclerosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, autoimmune vasculitis, sepsis, and chronic obstructive pulmonary disease.

In an even more preferable embodiment, the disease or disorder is selected from transplant rejection, rheumatoid arthritis, psoriatic arthritis, multiple sclerosis, asthma, inflammatory bowel disease, systemic lupus, erythematosis, and psoriasis.

In addition, in accordance with the present invention a method of treating a disease associated with AP-1-induced and/or NF-κB-induced transcription (particularly AP-1-induced transcription) is provided wherein a compound of formula I of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

In still another embodiment, pharmaceutical combinations are contemplated comprising a compound as defined in Claim 1, an enantiomer, diastereomer, or tautomer thereof, or a prodrug ester thereof, or a pharmaceutically-acceptable salt thereof, and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid-lowering agent is an MTP inhibitor, an HMG CoA reductase inhibitor, a squalene synthetase inhibitor, a fabric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

More preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-H039242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid-lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment are meant to be combined with any and all other elements from any of the embodiments to describe additional embodiments.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Compounds of formula I of the invention are prepared as described by the schemes and examples below. In the schemes the various groups E, F, G, M, $M_a$, Q, Z, $Z_a$, $R_4$, X, $R_{5a}$, $R_6$ and $R_7$ correspond to those described above.

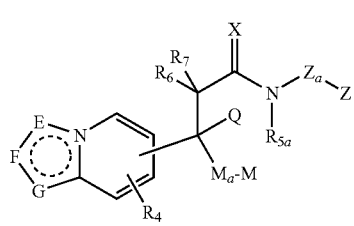

I

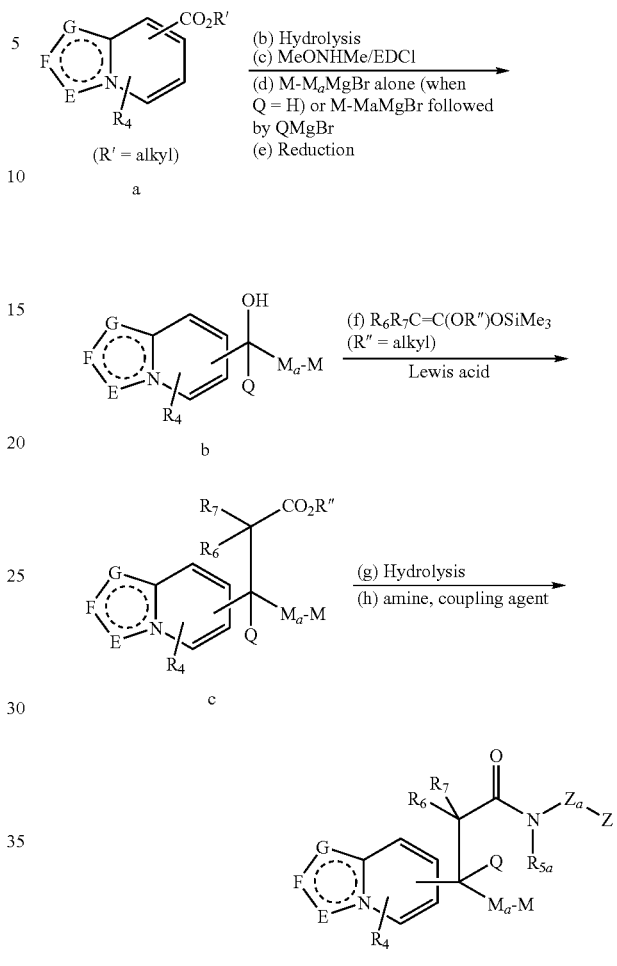

Scheme 1 illustrates a typical method for synthesizing compounds of formula I (where X=O). Compounds of type a are either commercially available or can be prepared by methods known in the art (for example, see *Youji Huaxue*, 23(2):173-175 (2003); *Chinese Chemical Letters*, 11(11):949-950 (2000); *Chem. Pharm. Bull.*, 44(5):991-999 (1996)) or as detailed below in the experimental section. Hydrolysis of the ester a can be accomplished by a variety of methods known in the art (for example see, in Larock, R. C., *Comprehensive Organic Transformations*, $2^{nd}$ Edition, VCH Publishers, Inc. (1999)). Conversion of the acid to the Weinreb amide followed by the addition of the appropriate Grignard, zinc or lithium reagent gives the ketone b or the alcohol b. In cases where Q=H, the ketone b can be reduced to the alcohol b by methods known in the art. Treatment of the alcohol b with the appropriate silyl enolether provides the ester c. Hydrolysis of the ester c followed by coupling with an amine affords compounds of formula I (where X=O). The coupling of the acid with an amine can be done by one of the many methods of amidation well know to those skilled in the art [for example using 1-hydroxybenzotriazole, N-ethyl-N, N-diisopropylamine and 1-(3-dimethylaminopropyl)-3-ethylcarbodiimide hydrochloride (EDCl) and anhydrous acetonitrile as the solvent].

SCHEME 2

Synthesis of Compounds of Formula I

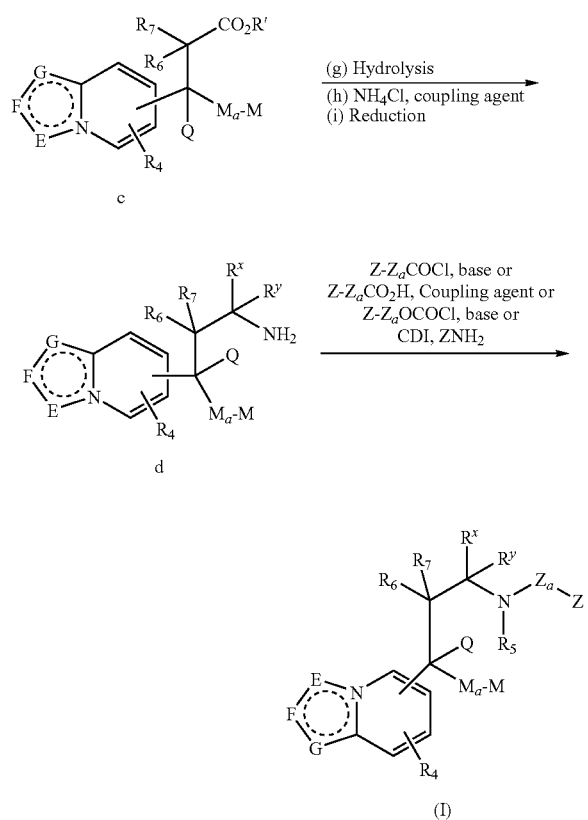

Scheme 2 shows one way of making compounds of Formula I, where X=(R$^x$/R$^y$) (for example where R$^x$,R$^y$=H). Hydrolysis of the ester c as described above, followed by coupling with ammonium chloride in the presence of a coupling agent [for example 1-(3-dimethylaminopropyl)-3-ethylcarbodiimide hydrochloride (EDCI)] affords the intermediate amide which on reduction affords the amine d. Reduction of the amide can be accomplished by a variety of methods known in the art (for example see, in Larock, R. C., *Comprehensive Organic Transformations*, 2$^{nd}$ Edition, VCH Publishers, Inc. (1999)). Coupling of the amine d with an acid, acid chloride, chloroformate or an amine and CDI (1,1'-carbonyldiimidazole) affords the corresponding amide, carbamate and urea I respectively. Various modifications to these methods may be envisioned by those skilled in the art to achieve results to that of the authors given below.

Schemes 3 to 5 show some examples of making the intermediate acid derivatives c that can be converted to compounds of formula I by a variety of methods mentioned above.

Scheme 3 shows how Q and M can be introduced to form a cyclic or acyclic benzylic quaternary carbon using the method of Robichaud et al. (*Synth. Commun.*, 31:679-684 (2001)). Metal-halogen exchange of the iodoheterocycle e followed by treatment with CuI forms a cuprate that undergoes conjugate addition to Meldrum's acid alkylidenes (made using the procedure of Baty, *J. Org. Chem.*, 34:3295-3302 (1969)). Hydrolysis of the ketal f protecting group with acid followed by thermal decarboxylation provides the acid g.

SCHEME 3

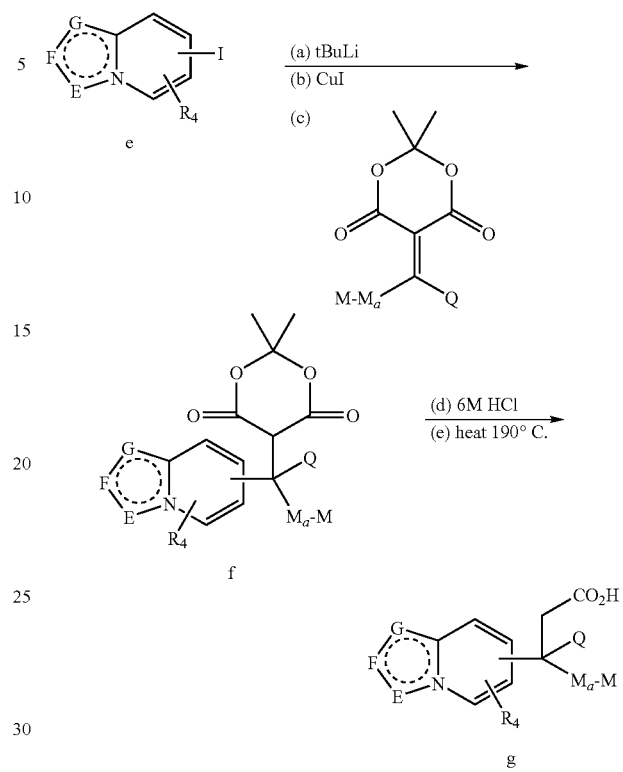

Another means of making intermediates enroute to compounds of Formula I is shown in Scheme 4. Metal-halogen exchange of compound e to form a Grignard reagent followed by treatment with a ketone or aldehyde provides compound f which is transposed to compound i as previously described in Scheme 1.

SCHEME 4

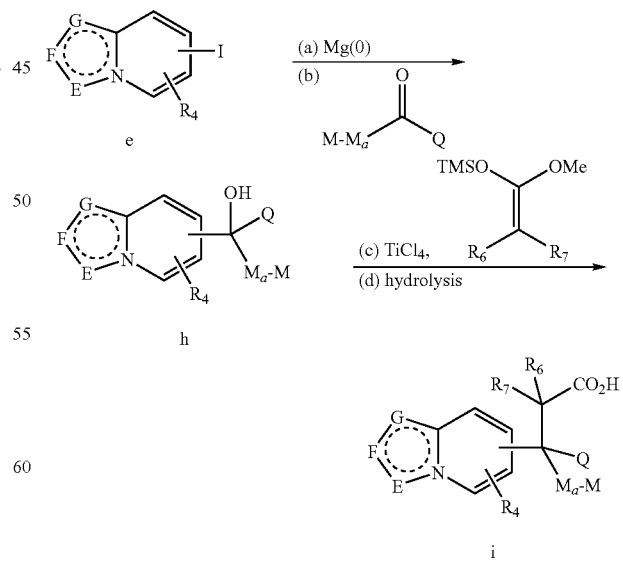

Scheme 5 illustrates a synthetic method for a precursor to Formula I wherein Q and R$_6$ form a ring (cyclopropyl shown here). Treatment of compound i with MeMgBr yields a tertiary alcohol which can be dehydrated in hot glacial acetic acid to olefin k. Rhodium-carbenoid addition provides a cyclopropyl ester which can be hydrolyzed to give acid l.

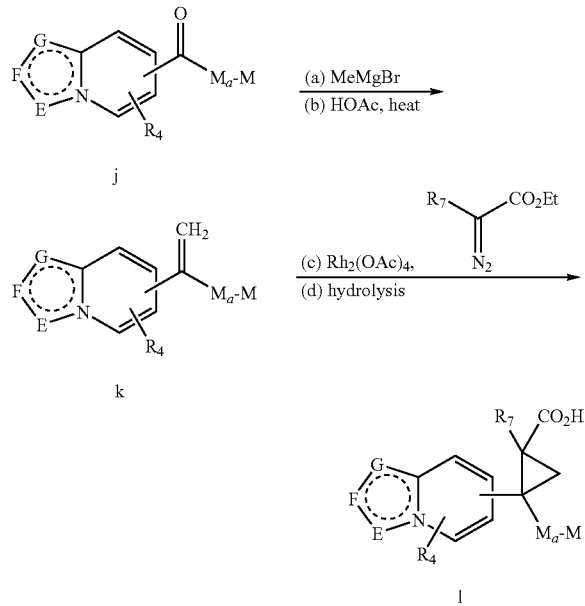

Protecting Groups for the Heterocyclic Core

It should be understood that protecting groups may be utilized as appropriate throughout synthetic Schemes 1 to 5 above. Common protecting groups for amine-containing heterocycles (where E, F, or G in Formula I are nitrogen, for example, indole, indazole, benzimidazole, and the like) are ureas, sulfonamides, carbamates, and alkyl groups (such as 4-methoxybenzyl). The judicious use of protecting groups is known to one skilled in the art and described in Greene et al., *Protecting Groups in Organic Synthesis*, Vol. 3.

Definitions

The following are definitions of terms used in this specification and appended claims. The initial definition provided for a group or term herein applies to that group or term throughout the specification and claims, individually or as part of another group, unless otherwise indicated.

The term "alkyl" alone or as part of another group refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl.

"Alkyl" includes "unsubstituted" and "substituted alkyl" where the alkyl may be substituted with any of the substituents for substituted alkyl set out below.

The term "substituted alkyl" refers to an alkyl group as defined above having one, two, or three substituents independently selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$ and $R_b$ are the same or different and are independently selected from hydrogen, alkyl, alkenyl, $CO_2H$, $CO_2$(alkyl), $C_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of ($C_{1-6}$)alkyl, ($C_{2-6}$)alkenyl, hydroxy, halogen, cyano, nitro, $CF_3$, $O(C_{1-6}$ alkyl), $OCF_3$, $C(=O)H$, $C(=O)(C_{1-6}alkyl)$, $CO_2H$, $CO_2$($C_{1-6}$alkyl), $NHCO_2(C_{1-6}alkyl)$, —$S(C_{1-6}alkyl)$, —$NH_2$, $NH(C_{1-6}alkyl)$, $N(C_{1-6}alkyl)_2$, $N(CH_3)_3^+$, $SO_2(C_{1-6}alkyl)$, —$NHC(=O)alkyl$, $C(=O)(C_{1-4}alkylene)NH_2$, $C(=O)$ ($C_{1-4}alkylene)NH(alkyl)$, $C(=O)(C_{1-4}alkylene)N(C_{1-4} alkyl)_2$, $C_{3-7}$cycloalkyl, phenyl, benzyl, phenylethyl, phenyloxy, benzyloxy, naphthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below and/or as defined for substituted alkyl.

One skilled in the field will understand that, when the designation "$CO_2$" is used herein, this is intended to refer to the group

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl ($C_{0-4}$)alkyl includes a substituted lower alkyl having at least one aryl substituent and also includes an aryl directly bonded to another group, i.e., aryl($C_0$)alkyl.

The term "alkenyl" (which includes unsubstituted or substituted alkenyl) alone or as part of another group refers to straight or branched chain hydrocarbon groups having 2 to 12 carbon atoms and at least one double bond. Alkenyl groups of 2 to 6 carbon atoms and having one double bond are most preferred.

The term "alkynyl" (which includes unsubstituted or substituted alkynyl) alone or as part of another group refers to straight or branched chain hydrocarbon groups having 2 to 12 carbon atoms and at least one triple bond. Alkynyl groups of 2 to 6 carbon atoms and having one triple bond are most preferred.

The term "alkylene" (which includes unsubstituted or substituted alkylene) alone or as part of another group refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" (which includes unsubstituted and "substituted heteroalkylene") alone or as part of another group is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—, —O—(CH$_2$)$_{1-5}$S(=O)—CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in C$_{2-3}$heteroalkylene, the subscript refers to the number of carbon atoms in the group in addition to heteroatoms. Thus, for example, a C$_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or A$_1$-Q-A$_2$-R$_h$, wherein A$_1$ is a bond, C$_{1-2}$alkylene, or C$_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, C$_{1-3}$alkylene, C$_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteroalkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an unsubstituted alkyl or substituted alkyl group as defined above having one or two oxygen atoms (—O—) in the alkyl chain. For example, the term "alkoxy" includes the groups —O—C$_{1-12}$alkyl, —(C$_{1-6}$alkylene)-O—C$_{1-6}$alkyl, —(C$_{1-4}$alkylene-O—C$_{1-4}$alkylene)-O—C$_{1-4}$alkyl, and so forth.

The term "thioalkyl" or "alkylthio" refers to an unsubstituted alkyl or substituted alkyl group as defined having one or two sulfur atoms in the alkyl chain. For example, the term "thioalkyl" or "alkylthio" includes the groups —S—C$_{1-12}$alkyl, —(S—C$_{1-6}$alkylene)-S—C$_{1-6}$alkyl, and so forth.

The terms "aminoalkyl" or "alkylamino" refer to an unsubstituted alkyl or substituted alkyl group as defined above having one or two nitrogen (—NR—) atoms in the alkyl chain. For example, the term "aminoalkyl" includes the groups —NR—C$_{1-12}$alkyl, —NR—C$_{1-6}$alkylene-NR—C$_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent C$_{1-2}$-aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl is an aminoalkyl having one to four carbon atoms.

"Amino" refers to the group NH$_2$.

The term "substituted amino" alone or as part of another group refers to the group —NR$_a$R$_b$ (or other substituent groups other than R$_a$ or R$_b$ linked to an N atom) wherein the groups R$_a$ and R$_b$ or other substituent groups are defined above in the definition of substituted alkyl groups.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—C$_{1-12}$alkyl, —C$_{1-6}$alkylene-O—C$_{1-6}$alkyl, —C$_{1-4}$alkylene-O—C$_{1-4}$alkylene-O—C$_{1-4}$alkyl, whereas a bivalent alkoxy includes groups such as —O—C$_{1-12}$alkylene-, —C$_{1-6}$alkylene-O—C$_{1-6}$alkylene-, —C$_{1-4}$alkylene-O—C$_{1-4}$alkylene-O—C$_{1-4}$alkylene-, and so forth.

The term "carbonyl" is intended to designate the group —C(O)—.

It should be understood that the selections for alkoxy, thioalkyl, and aminoalkyl will be made by one skilled in the field to provide stable compounds. Thus, for example, in compounds of formula I, when R$_5$, R$_6$, R$_7$ or R$_8$ is attached to a nitrogen atom (N*) of ring B and is selected from an alkoxy or alkylthio group, the alkoxy and alkylthio groups will have at least one carbon atom bonded directly to ring B (at N*), with the oxygen or sulfur atoms being at least one atom away from said nitrogen atom.

The term "acyl" alone or as part of another group refers to a carbonyl group linked to an organic radical, more particularly, the group C(=O)R$_e$, as well as the bivalent groups —C(=O) or —C(=O)R$_e$—, which are linked to organic radicals or a ring in compounds of formula I. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of formula I, when it is recited that R$_1$ to R$_8$ can be "acyl," this is intended to encompass a selection for R$_1$ to R$_8$ of —C(=O) and also the groups —C(=O)R$_e$— or —R$_e$C(=O)—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" alone or as part of another group refers to a carboxy group

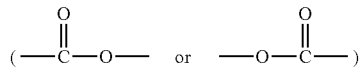

linked to an organic radical (CO$_2$R$_e$), as well as the bivalent groups —CO$_2$—, CO$_2$R$_e$— which are linked to organic radicals in compounds of formula I, wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.). Accordingly, "alkoxycarbonyl," is intended to encompass the groups CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" alone or as part of another group refers to the group C(=O)NR$_a$R$_b$ (or other R groups other than R$_a$ or R$_b$ linked to an N atom), wherein the groups R$_a$ and R$_b$ are defined as recited above in the definition for substituted alkyl groups.

The term "sulfonyl" alone or as part of another group refers to a sulfoxide group linked to an organic radical in compounds of formula I, more particularly, the monovalent group S(O)$_{1-2}$—R$_e$, or the bivalent group —S(O)$_{1-2}$— linked to organic radicals in compounds of formula I. Accordingly, in compounds of formula I, "sulfonyl," is intended to encompass —S(=O) or SO$_2$— as well as the groups —S(=O)R$_e$—, —R$_e$S(=O)—, —SO$_2$R$_e$—, or —R$_e$SO$_2$—, wherein in this instance, the group R$_e$ will be selected from those recited above for acyl and alkoxycarbonyl groups.

The term "sulfonamidyl" alone or as part of another group refers to the group —S(O)$_2$NR$_a$R$_b$ (or other R groups other than R$_a$ or R$_b$ linked to an N atom), wherein R$_a$ and R$_b$ are as defined above for substituted alkyl groups. Additionally, the sulfonamidyl group may be bivalent, in which case one of the groups R$_a$ and R$_b$ will be a bond. Thus, in compounds of formula I, sulfonamidyl is intended to mean the group —S(O)$_2$NR$_a$—.

The term "cycloalkyl" alone or as part of another group (which includes unsubstituted cycloalkyl or substituted cycloalkyl) refers to fully saturated and partially unsaturated hydrocarbon rings of 3 to 15, preferably 3 to 10 carbon atoms. Accordingly, the term "cycloalkyl" is intended to include a cycloalkenyl (e.g., cyclohexenyl) ring. The term "cycloalkyl" includes monocyclic, bicyclic and tricyclic ring, such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, cycloalkyl, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)$_2$.

Accordingly, in compounds of formula I, the term "cycloalkyl" includes cyclopropyl, cyclobutyl, cyclopentyl, cyclohexyl, cycloheptyl, cyclooctyl, etc., as well as the following ring systems,

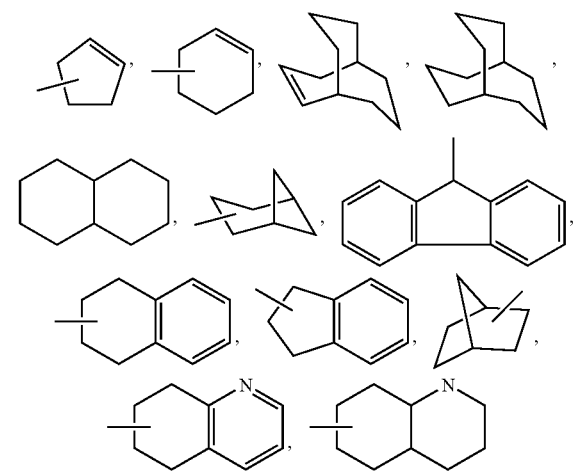

and the like, which optionally may be substituted at any available atoms of the ring(s). Preferred cycloalkyl groups include cyclopropyl, cyclobutyl, cyclopentyl, cyclohexyl,

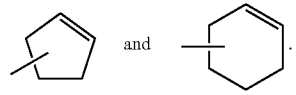

The term "halo" or "halogen" alone or as part of another group refers to chloro, bromo, fluoro and iodo.

The term "haloalkyl" alone or as part of another group means a substituted alkyl having one or more halo substituents. For example, "haloalkyl" includes mono, bi, and trifluoromethyl.

The term "haloalkoxy" alone or as part of another group means an alkoxy group having one or more halo substituents. For example, "haloalkoxy" includes OCF$_3$.

The term "aryl" alone or as part of another group (which includes unsubstituted aryl and substituted aryl) refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —OC$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above, or any of the substituents for alkyl set out hereinbefore. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to four, preferably one or two of ($C_{1-4}$)alkyl, ($C_{2-4}$alkenyl, halogen, hydroxy, cyano, nitro, $CF_3$, $O(C_{1-4}$alkyl), $OCF_3$, $C(=O)$H, $C(=O)(C_{1-4}$alkyl), $CO_2H$, $CO_2(C_{1-4}$alkyl), $NHCO_2(C_{1-4}$alkyl), $—S(C_{1-4}$alkyl), $—NH_2$, $NH(C_{1-4}$alkyl), $N(C_{1-4}$alkyl)$_2$, $N(C_{1-4}$alkyl)$_3^+$, $C(=O)NH_2$, $SO_2(C_{1-4}$alkyl), $C(=O)(C_{1-4}$alkylene)$NH_2$, $C(=O)(C_{1-4}$alkylene)NH(alkyl), and/or $C(=O)(C_{1-4}$alkylene)$N(C_{1-4}$alkyl)$_2$.

Thus, examples of aryl groups include:

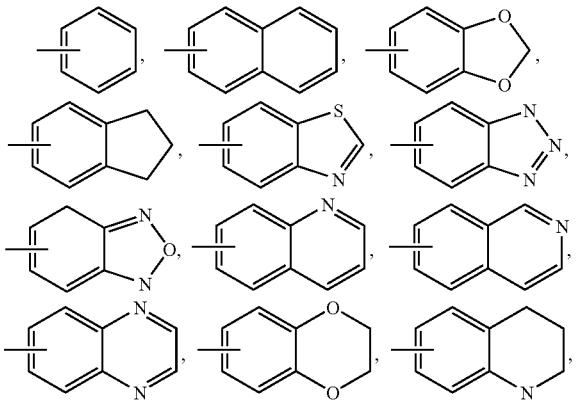

and the like, which optionally may be substituted at any available carbon or nitrogen atom. A preferred aryl group is optionally-substituted phenyl.

The terms "heterocyclo" or "heterocyclic" or "cycloheteroalkyl" alone or as part of another group refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $—NR_aR_b$, $—N(alkyl)_3^+$, $—NR_aSO_2$, $—NR_aSO_2R_c$, $—SO_2R_c—SO_2NR_aR_b$, $—SO_2NR_aC(=O)$ $R_b$, $SO_3H$, $—PO(OH)_2$, $—C(=O)R_a$, $—CO_2R_a$, $—C(=O)$ $NR_aR_b$, $—C(=O)(C_{1-4}$alkylene)$NR_aR_b$, $—C(=O)NR_a$ $(SO_2)R_b$, $—CO_2(C_{1-4}$alkylene)$NR_aR_b$, $—NR_aC(=O)R_b$, $—NR_aCO_2R_b$, $—NR_a(C_{1-4}$alkylene)$CO_2R_b$, $=N—OH$, $=N—O$-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of ($C_{1-4}$alkyl, ($C_{2-4}$)alkenyl, halogen, hydroxy, cyano, nitro, $CF_3$, $O(C_{1-4}$alkyl), $OCF_3$, $C(=O)H$, $C(=O)$ $(C_{1-4}$alkyl), $CO_2H$, $CO_2(C_{1-4}$alkyl), $NHCO_2(C_{1-4}$alkyl), $—S(C_{1-4}$alkyl), $—NH_2$, $NH(C_{1-4}$alkyl), $N(C_{1-4}$alkyl)$_2$, $N(C_{1-4}$alkyl)$_3^+$, $SO_2(C_{1-4}$alkyl), $C(=O)(C_{1-4}$alkylene)$NH_2$, $C(=O)(C_{1-4}$alkylene)NH(alkyl), and/or $C(=O)(C_{1-4}$alkylene)$N(C_{1-4}$alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolidinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula I include

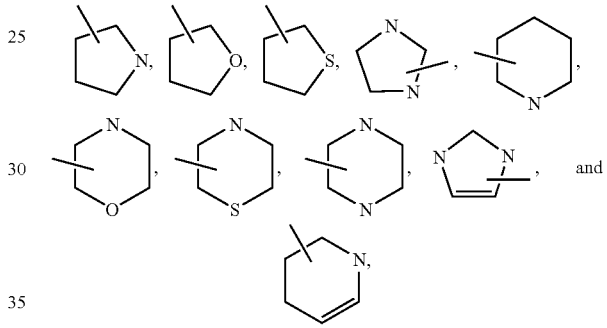

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $—NR_aR_b$, $—N(alkyl)_3^+$, $—NR_aSO_2$, $—NR_aSO_2R_c$, $—SO_2R_c—SO_2NR_aR_b$, $—SO_2NR_aC(=O)R_b$, $SO_3H$, $—PO$ $(OH)_2$, $—C(=O)R_a$, $—CO_2R_a$, $—C(=O)NR_aR_b$, $—C(=O)$ $(C_{1-4}$alkylene)$NR_aR_b$, $—C(=O)NR_a(SO_2)R_b$, $—CO_2(C_{1-4}$ alkylene)$NR_aR_b$, oxo(=O), $—NR_aC(=O)R_b$, $—NR_aCO_2R_b$, $—NR_a(C_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of ($C_{1-4}$alkyl), ($C_{2-4}$) alkenyl, halogen, hydroxy, cyano, nitro, $CF_3$, $O(C_{1-4}$alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), —$S(C_{1-4}$alkyl), —$NH_2$, $NH(C_{1-4}$alkyl), $N(C_{1-4}$alkyl)$_2$, $N(C_{1-4}$alkyl)$_3^+$, $SO_2(C_{1-4}$alkyl), $C(=O)(C_{1-4}$alkylene)$NH_2$, $C(=O)(C_{1-4}$alkylene)NH(alkyl), and/or $C(=O)(C_{1-4}$alkylene)$N(C_{1-4}$alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula I, preferred heteroaryl groups include

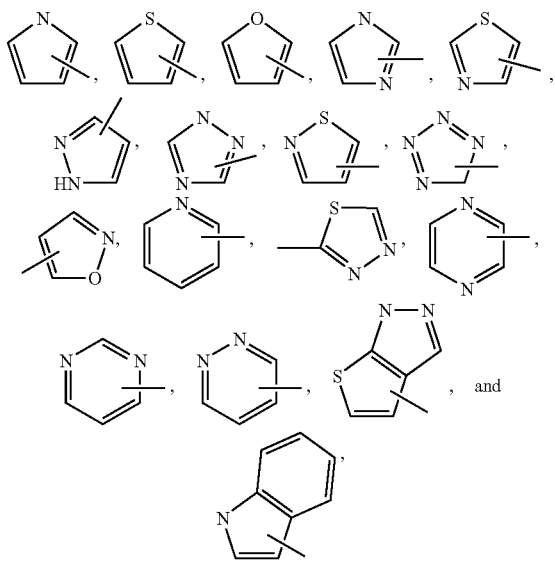

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "prodrug" denotes a compound which, upon administration to a subject, undergoes chemical conversion by metabolic or chemical processes to yield a compound of the formula I, and/or a salt and/or solvate thereof. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

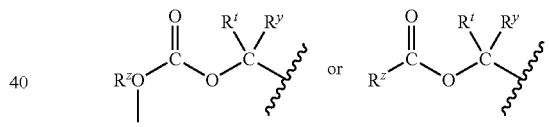

wherein $R^z$, $R^t$ and $R^y$ are H, alkyl, aryl or arylalkyl; however, $R^zO$ cannot be HO.

Examples of such prodrug esters include

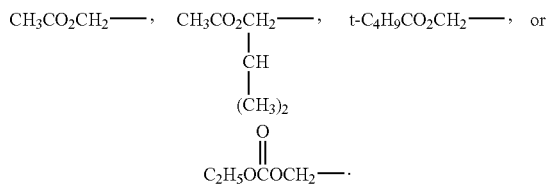

Other examples of suitable prodrug esters include

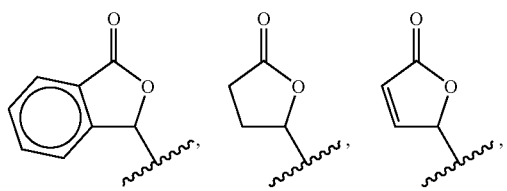

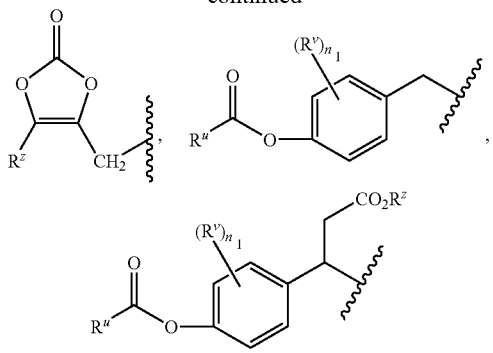

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, 112:309-396, edited by K. Widder et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8:1-38 (1992).

The term "tautomer" refers to compounds of the formula I and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g., hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g., CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf).

The hypolipidemic agent or lipid-lowering agent or lipid modulating agents which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

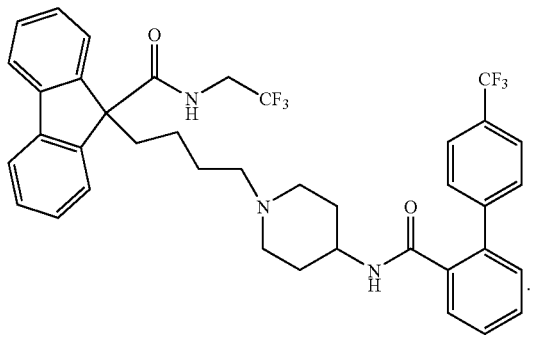

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 642-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31(10):1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey and Volante, *J. Am. Chem. Soc.*, 98:1291-1293 (1976), phosphinylphosphonates reported by McClard, R. W. et al., *J. Am. Chem. Soc.*, 109:5544 (1987), and cyclopropanes reported by Capson, T. L., Ph.D., dissertation, Dept. Med. Chem. U. of Utah, Abstract, Table of Contents, pp. 16, 17, 40-43, 48-51, Summary (June 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, *Drugs of the Future*, 24:9-15 (1999), (Avasimibe); Nicolosi et al., "The ACAT inhibitor, Cl-1011 is effective in the prevention and regression of aortic fatty streak area in hamsters", *Atherosclerosis* (Shannon, Irel.), 137(1): 77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.* 16(1):16-30 (1998); Smith, C. et al., "RP 73163: a bioavailable alkylsulfinyl-diphenylimidazole ACAT inhibitor", *Bioorg. Med. Chem. Lett.,* 6(1):47-50 (1996); Krause et al., "ACAT inhibitors: physiologic mechanisms for hypolipidemic and anti-atherosclerotic activities in experimental animals", *Inflammation: Mediators Pathways,* Publisher: CRC, Boca Raton, Fla., Editor(s): Ruffolo, Robert R., Jr., Hollinger, Mannfred A., pp. 173-198 (1995); Sliskovic et al., "ACAT inhibitors: potential anti-atherosclerotic agents", *Curr. Med. Chem.,* 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", *Chemtracts: Org. Chem.* 8(6):359-362 (1995), or TS-962 (acetamide, N[2,6-bis(1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis,* 115:45-63 (1995) and *J. Med. Chem.,* 41:973 (1998).

The hypolipidemic agent may be an ileal Na+/bile acid cotransporter inhibitor such as disclosed in *Drugs of the Future,* 24:425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physicians' Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physicians' Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al., "Attenuation of diet-induced atherosclerosis in rabbits with a highly selective 15-lipoxygenase inhibitor lacking significant antioxidant properties", *Brit. J. Pharmacology,* 120:1199-1206 (1997), and Cornicelli et al., "15-Lipoxygenase and its Inhibition: A Novel Therapeutic Target for Vascular Disease", *Current Pharmaceutical Design,* 5:11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-1,4-bis-4-[(3,5-dioxo-1,2,4-oxadiazolidin-2-yl-methyl)]-phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1-36) amide, GLP-1 (7-36) amide, GLP-1 (7-37) (as disclosed in U.S. Pat. No. 5,614,492 to Habener, the disclosure of which is incorporated herein by reference), as well as AC2993 (exenatide) (Amylin) and LY-315902 (8-37—glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-H039242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]- (Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma Effect on PPAR alpha Activation on Abnormal Lipid Metabolism in Liver of Zucker Fatty Rats", *Diabetes*, 47:1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., *Biochemistry*, 38(36):11597-11603, (1999), TSL-225 (tryptophyl-1,2,3,4-tetrahydro-isoquinoline-3-carboxylic acid (disclosed by Yamada et al., *Bioorg. & Med. Chem. Leu.*, 8:1537-1540 (1998), 2-cyanopyrrolidides and 4-cyanopyrrolidides as disclosed by Ashworth et al., *Bioorg. & Med. Chem. Leu.*, 6(22):1163-1166 and 2745-2748 (1996) employing dosages as set out in the above references.

The meglitinide which may optionally be employed in combination with the compound of formula I of the invention may be repaglinide, nateglinide (Novartis) or KAD1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benzenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al. mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol., 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C. A. 102:72588v and Jap. J. Pharmacol., 40:373 (1986); Ciba-Geigy's CGS14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res., 39:671 (1986); 40:543 (1986); ramipril (Hoechst) disclosed in Euro. Patent No. 79-022 and Curr. Ther. Res., 40:74 (1986); Ru 44570 (Hoechst) disclosed in Arzneimittelforschung, 34:1254 (1985), cilazapril (Hoffman-LaRoche) disclosed in J. Cardiovasc. Pharmacol., 9:39 (1987); R 31-2201 (Hoffman-LaRoche) disclosed in FEBS Lett., 165:201 (1984); lisinopril (Merck), indalapril (delapril) disclosed in U.S. Pat. No. 4,385,051; indolapril (Schering) disclosed in J. Cardiovasc. Pharmacol., 5:643, 655 (1983), spirapril (Schering) disclosed in Acta. Pharmacol. Toxicol., 59(Supp. 5):173 (1986); perindopril (Servier) disclosed in Eur. J. Clin. Pharmacol., 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1, 2,3,4-tetrahydro-6,7-dimethoxy-3-isoquinolinecarboxylic acid HCl) disclosed in Pharmacologist, 26:243, 266 (1984), WY-44221 (Wyeth) disclosed in J. Med. Chem., 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat ([S—(R*,R*)]-hexahydro-6-[(2-mercapto-1-oxo-3-phenylpropyl)amino]-2, 2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physicians' Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of the examples are inhibitors of AP-1 activity and/or compete with known ligands of the glucocorticoid receptor.

Compounds of the invention, including the compounds described in the examples hereof, have been tested in at least one of the assays described below and have glucocorticoid receptor (GR)/Dexamethasone (Dex) inhibition activity and/or AP-1 inhibition activity.

Assays

GR Binding Assay
Glucocorticoid Receptor Binding Assay

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e. Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity, with dexamethasone being 100% and no inhibition being 0%. Test compounds were analyzed in the concentration range from 8.5E-05 µM to 5 µM.

Cellular Transrepressional Assay

To measure the ability of test molecules to inhibit AP-1 induced transcriptional activity, an A549 cell was utilized which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity. In the absence of an EC50 the maximum % inhibition recorded is the inhibition of AP-1 at a compound concentration of 10 micromolar.

Other reporters and cell lines also may be used in a cellular transrepressional assay. A similar assay is performed in which NF-κB activity is measured. A plasmid containing NF-κB DNA binding sites is used, such as pNF-κB-Luc, (Stratagene, LaJolla Calif.), and PMA or another stimulus, such as TNF-α or lipopolysaccharide, is used to activate the NF-κB pathway. NF-κB assays similar to that described in Yamamoto K. et al., *J. Biol. Chem.*, 270(52):31315-31320 (Dec. 29, 1995) may be used.

The cellular transrepressional assays described above may be used to measure transrepression by any NHR. One of skill in the art will understand that assays may require the addition of components, such as a stimulus (e.g., PMA, lipopolysaccharide, TNF-α, etc.) which will induce transcription mediated by AP-1 or NF-κB.

Additionally, AR mediated transrepression may be measured by the assay described in Palvimo. J. J. et al., *J. Biol. Chem.*, 271(39):24151-24156 (Sep. 27, 1996), and PR mediated transrepression may be measured by the assay described in Kalkhoven E. et al., *J. Biol. Chem.*, 271(11):6217-6224 (Mar. 15, 1996).

ABBREVIATIONS

The following abbreviations are employed in the following Examples:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide HOAc or AcOH=acetic acid
TFA=trifluoroacetic acid
TFAA=trifluoroacetic anhydride
i-Pr$_2$NEt=diisopropylethylamine
Et$_3$N=triethylamine
NMM=N-methyl morpholine
DMAP=4-dimethylaminopyridine
NaBH$_4$=sodium borohydride
NaBH(OAc)$_3$=sodium triacetoxyborohydride
DIBALH=diisobutyl aluminum hydride
LAH or LiAlH$_4$=lithium aluminum hydride
n-BuLi=n-butyllithium
LDA=lithium diisopropylamide
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris(dimethylamino) phosphonium hexafluorophosphate
NaN(TMS)$_2$=sodium hexamethyldisilazide or sodium bis(t-rimethylsilyl)amide
Ph$_3$P=triphenylphosphine
Pd(OAc)$_2$=Palladium acetate
(Ph$_3$P)$_4$Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
Reverse phase HPLC=reverse phase high performance liquid chromatography, using a YMC ODS S5 column and a binary solvent A/solvent B eluents
Solvent A=10% MeOH–90% H$_2$O–0.1% TFA
Solvent B=90% MeOH–10% H$_2$O–0.1% TFA
LC/MS=high performance liquid chromatography/mass spectrometry
MS or Mass Spec=mass spectrometry NMR=nuclear magnetic resonance
NMR spectral data: s=singlet; d=doublet; m=multiplet; br=broad; t=triplet
mp=melting point

EXAMPLES

The following Examples illustrate some of the preferred embodiments of the inventive compounds and starting materials, and are not intended to limit the scope of the claims.

Example 1

2,2-Dimethyl-3-phenyl-3-(3-phenylH-imidazo[1,5-a]pyridin-7-yl)-N-(1,3,4-thiadiazol-2-yl)propanamide

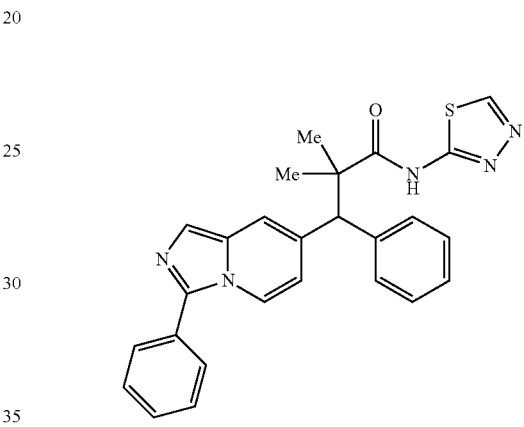

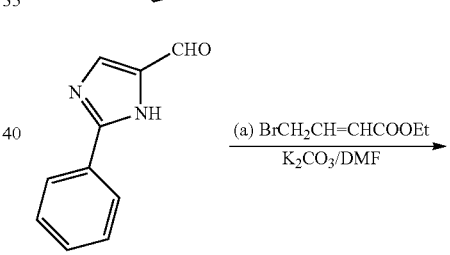

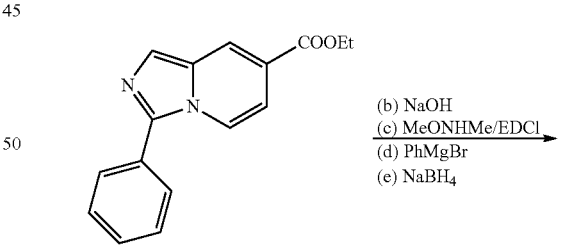

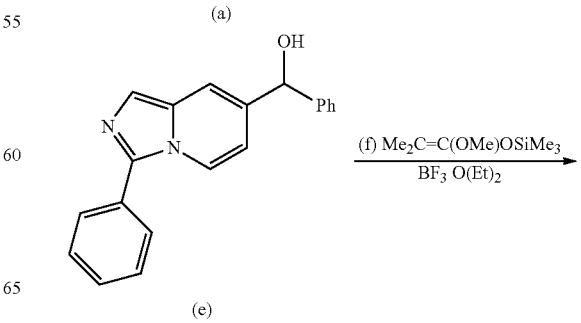

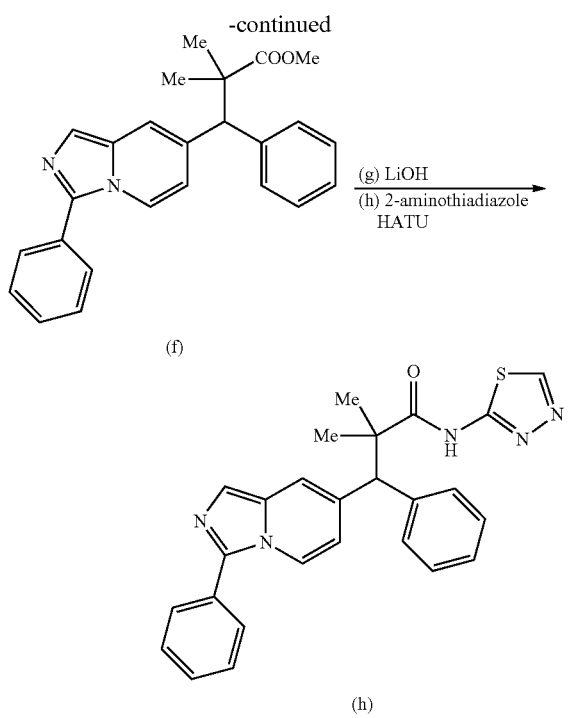

(a) To a stirred mixture of 2-phenyl-1H-imidazole-5-carbaldehyde (3.0 g, 17 mmol), anhydrous potassium carbonate (2.8 g, 20 mmol), and anhydrous DMF (12 mL) was added ethyl 4-bromocrotonate (2.4 mL, 17 mmol) at rt under argon. The reaction mixture was stirred at 80° C. for 15 hr and 85° C. for 6 hr. The mixture was concentrated and partitioned between water (50 mL) and ethyl acetate (50 mL). The aqueous layer was separated and extracted with ethyl acetate (2×30 mL). The combined ethyl acetate solutions were dried ($Na_2SO_4$) and concentrated. Silica gel flash chromatography (0-100% ethyl acetate in hexanes) gave ethyl 3-phenylH-imidazo[1,5-a]pyridine-7-carboxylate (1.3 g, 4.9 mmol, 29% yield) as a liquid. MS found: $(M+H)^+=267.27$.

(b) To a stirred solution of ethyl 3-phenylH-imidazo[1,5-a]pyridine-7-carboxylate (1.3 g, 4.9 mmol) in ethanol (95%, 20 mL) was added aqueous sodium hydroxide solution (2N, 20 mL, 40 mmol). The reaction mixture was stirred at room temperature for 1 hour and concentrated under reduced pressure to remove ethanol. The residue was neutralized with aqueous hydrochloric acid solution (6N, ca 3.3 mL). The mixture was heated to 90° C. and then cooled. The solid was filtered, washed with water, and dried to give 3-phenylH-imidazo[1,5-a]pyridine-7-carboxylic acid (1.1 g, 4.5 mmol, 92% yield) as a yellow solid. MS found: $(M+H)^+=239.18$.

(c) To a stirred solution of 3-phenylH-imidazo[1,5-a]pyridine-7-carboxylic acid (1.1 g, 4.5 mmol), 1-hydroxybenzotriazole (0.61 g, 4.5 mmol), N,O-dimethylhydroxylamine hydrochloride (0.88 g, 9 mmol), diisopropylethylamine (4.7 mL, 27 mmol) in anhydrous acetonitrile (15 mL) was added N-(3-dimethylamino-propyl)-N'-ethylcarbodiimide hydrochloride (1.7 g, 9.0 mml). After the reaction mixture was stirred at room temperature for 1.5 hours and 70° C. for 1.5 hours, it was concentrated. The residue was dissolved in ethyl acetate (100 mL), washed with saturated aqueous sodium bicarbonate solution (2×20 mL), dried ($Na_2SO_4$), filtered through a pad of silica gel, and concentrated to give N-methoxy-N-methyl-3-phenylH-imidazo[1,5-a]pyridine-7-carboxamide (1.3 g, 4.5 mmol, 100% yield). MS found: $(M+H)^+=282.29$.

(d) To a stirred solution of N-methoxy-N-methyl-3-phenylH-imidazo[1,5-a]pyridine-7-carboxamide (1.3 g, 4.5 mmol) in anhydrous tetrahydrofuran (14 mL) was added phenylmagnesium bromide solution (3M in diethyl ether, 4.5 mL, 14 mmol) dropwise at 0° C. under argon. After the reaction mixture was stirred at 0° C. for 1.5 hr, saturated aqueous ammonium chloride solution (15 mL) was added to quench the reaction. The mixture was extracted with ethyl acetate (3×15 mL). The combined ethyl acetate extracts were dried ($Na_2SO_4$) and concentrated. Silica gel flash chromatography (0-100% ethyl acetate in hexanes) gave phenyl(3-phenylH-imidazo[1,5-a]pyridin-7-yl)methanone (1.0 g, 3.4 mmol, 76% yield) as a yellow solid. MS found: $(M+H)^+=299.29$.

(e) To a stirred solution of phenyl(3-phenylH-imidazo[1,5-a]pyridin-7-yl)methanone (1.0 g, 3.4 mmol) in THF (9 mL) and ethanol (9 mL) was added sodium borohydride (0.16 g, 4.2 mmol). After the reaction mixture was stirred at room temperature for 1.5 hours, saturated aqueous ammonium chloride solution (20 mL) was added slowly to quench the reaction. The mixture was concentrated under reduced pressure to remove organic solvents. The residue was extracted with ethyl acetate (3×20 mL). The combined ethyl acetate extracts were dried ($Na_2SO_4$), filtered through a pad of silica gel, and concentrated to phenyl(3-phenylH-imidazo[1,5-a]pyridin-7-yl)methanol (1.1 g, 3.6 mmol, 100% yield) as a solid. MS found: $(M+H)^+=301.30$.

(f) To a stirred solution of phenyl(3-phenylH-imidazo[1,5-a]pyridin-7-yl)methanol (1.1 g, 3.6 mmol) and (1-methoxy-2-methylprop-1-enyloxy)-trimethylsilane (4 mL, 20 mmol) in anhydrous dichloromethane (6 mL) was added boron trifluoride diethyl ether complex (1.9 mL, 15 mmol) dropwise at 0° C. under argon. After stirring at 0° C. for 5 min, room temperature for 4 hours, and 40° C. for 1 hour, the mixture was poured into a saturated aqueous sodium bicarbonate solution (40 mL) maintained at 0° C. The mixture was stirred well, extracted with dichloromethane (2×20 mL). The combined organic solutions were dried ($Na_2SO_4$) and concentrated. Silica gel flash chromatography (0-100% ethyl acetate in hexanes) gave methyl 2,2-dimethyl-3-phenyl-3-(3-phenylH-imidazo[1,5-a]pyridin-7-yl)propanoate (1.0 g, 2.6 mmol, 72% yield) as a colorless liquid. MS found: $(M+H)^+=385.38$.

(g) A mixture of methyl 2,2-dimethyl-3-phenyl-3-(3-phenylH-imidazo[1,5-a]pyridin-7-yl)propanoate (1.0 g, 2.6 mmol), lithium hydroxide monohydrate (1.3 g, 31 mmol), water (25 mL), and dioxane (25 mL) was stirred at 110° C. for 9 hr and at 100° C. overnight. The reaction mixture was cooled to room temperature and partitioned between water (20 mL) and diethyl ether (40 mL). The ether layer was reextracted with water (2×5 mL). The combined aqueous solutions were neutralized with 6N aqueous hydrochloric acid solution (4 mL) and aqueous 10% citric acid solution (8 mL) and extracted with ethyl acetate (3×30 mL). The combined ethyl acetate extracts were washed with brine (10 mL), dried ($Na_2SO_4$) and concentrated to give 2,2-dimethyl-3-phenyl-3-(3-phenylH-imidazo[1,5-a]pyridin-7-yl)propanoic acid (0.95 g, 2.6 mmol, 100% yield). MS found: $(M-H)^-=369.25$.

2,2-Dimethyl-3-phenyl-3-(3-phenylH-imidazo[1,5-a]pyridin-7-yl)propanoic acid was resolved into its enantiomers using a Chiralpak-AD column and a solvent system of $CO_2$/MeOH. Each enantiomer was converted into the corresponding amides using the following procedure.

(h) To a stirred solution of 2,2-dimethyl-3-phenyl-3-(3-phenylH-imidazo[1,5-a]pyridin-7-yl)propanoic acid (33 mg, 0.089 mmol), 2-amino-1,3,4-thiadiazole (27 mg, 0.27 mmol), and diisopropylethylamine (0.062 mL, 0.36 mmol) in anhydrous DMF (0.4 mL) was added HATU (136 mg, 0.36 mmol) under argon. After stirring at room temperature overnight and 80° C. for 20 minutes, the reaction mixture was concentrated. Purification using reverse phase HPLC (YMC S5 20×100 mm, 10 min. run, solvent A: 10% MeOH: 90% $H_2O$: 0.1%

TFA, solvent B: 90% MeOH, 10% $H_2O$, 0.1% TFA) gave 2,2-dimethyl-3-phenyl-3-(3-phenylH-imidazo[1,5-a]pyridin-7-yl)-N-(1,3,4-thiadiazol-2-yl)propanamide (22 mg, 0.039 mmol, 44% yield) as a trifluoroacetic acid salt. MS found: $(M+H)^+$=454.26. $^1$H-NMR (400 MHz, MeOD) δ ppm 8.91 (1H, s) 8.23 (1H, d, J=7.63 Hz) 7.88 (1H, s) 7.78 (1H, s) 7.66-7.73 (2H, m) 7.56-7.62 (3H, m) 7.30 (2H, d, J=7.12 Hz) 7.20-7.27 (3H, m) 6.85 (1H, d, J=8.14 Hz) 4.63 (1H, s) 1.39 (6H, d, J=24.92 Hz).

Example 2

N-(2,2-Dimethyl-3-phenyl-3-(3-phenylH-imidazo[1,5-a]pyridin-7-yl)propyl)-2,2,2-trifluoroacetamide

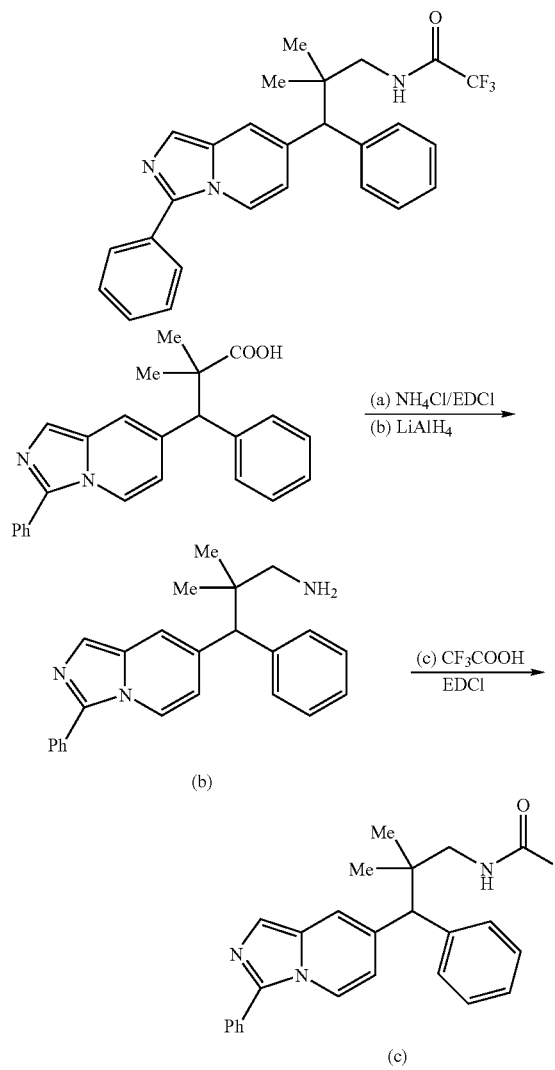

(a) To a stirred mixture of 2,2-dimethyl-3-phenyl-3-(3-phenylH-imidazo[1,5-a]pyridin-7-yl)propanoic acid (Example 1(g), 58 mg, 0.16 mmol), 1-hydroxy-benzotriazole (65 mg, 0.48 mmol), and anhydrous DMF (1 mL) was added N-(3-dimethylaminopropyl)-N'-ethylcarbodiimide hydrochloride (123 mg, 0.64 mmol). The reaction mixture was stirred at room temperature for 30 minutes before ammonium chloride (110 mg, 2 mmol) and diisopropylethylamine (0.3 mL) were added in sequence. The reaction mixture was stirred at room temperature for 5 hours and then concentrated under reduced pressure. The residue was partitioned between dichloromethane (5 mL) and water (5 mL). The aqueous layer was separated and extracted with dichloromethane (2×5 mL). The combined dichloromethane solutions were dried ($Na_2SO_4$) and concentrated. Silica gel flash chromatography (0-100% ethyl acetate in hexanes) gave 2,2-dimethyl-3-phenyl-3-(3-phenylH-imidazo[1,5-a]pyridin-7-yl)propanamide (53 mg, 0.14 mmol, 88% yield) as a solid. MS found: $(M+H)^+$=370.22.

(b) To a stirred solution of 2,2-dimethyl-3-phenyl-3-(3-phenylH-imidazo[1,5-a]pyridin-7-yl)propanamide (53 mg, 0.14 mmol) in anhydrous THF (3 mL) was added lithium aluminum hydride solution (1M in diethyl ether, 0.3 mL, 0.3 mmol) dropwise. After the reaction mixture was stirred at room temperature overnight under argon, aqueous sodium hydroxide solution (1N, 4 mL) was added slowly to quench the reaction. The mixture was extracted with diethyl ether (3×5 mL). The combined diethyl ether extracts were dried ($Na_2SO_4$ and $K_2CO_3$) and concentrated to give 2,2-dimethyl-3-phenyl-3-(3-phenylH-imidazo[1,5-a]pyridin-7-yl)propan-1-amine (47 mg, 0.13 mmol, 94% yield) as a solid. MS found: $(M+H)^+$=356.36.

(c) To a stirred mixture of 2,2-dimethyl-3-phenyl-3-(3-phenylH-imidazo[1,5-a]pyridin-7-yl)propan-1-amine (13 mg, 0.037 mmol), 1-hydroxy-benzotriazole (6 mg, 0.04 mmol), trifluoroacetic acid (0.08 mL, 1.1 mmol), pyridine (0.3 mL), and anhydrous dichloromethane (1 mL) was added N-(3-dimethylaminopropyl)-N'-ethylcarbodiimide hydrochloride (35 mg, 0.18 mmol). The reaction mixture was stirred at room temperature for 60 minutes before sodium bicarbonate (100 mg, 1.2 mmol) was added. After the reaction mixture was stirred at room temperature for 1 hour, saturated aqueous sodium bicarbonate solution (2 mL) was added to quench the reaction. The aqueous layer was separated and extracted with dichloromethane (2×2 mL). The combined dichloromethane solutions were dried ($Na_2SO_4$) and concentrated. Silica gel flash chromatography (0-100% ethyl acetate in hexanes) gave N-(2,2-dimethyl-3-phenyl-3-(3-phenylH-imidazo[1,5-a]pyridin-7-yl)propyl)-2,2,2-trifluoroacetamide (6 mg, 0.013 mmol, 36% yield) as a solid. MS found: $(M+H)^+$=452.11. $^1$H NMR (400 MHz, MeOD) δ ppm 8.95-9.02 (1H, m) 8.32 (1H, d, J=7.63 Hz) 7.90 (2H, s) 7.71-7.80 (2H, m) 7.58-7.64 (3H, m) 7.42 (2H, d, J=7.12 Hz) 7.25 (2H, t, J=7.38 Hz) 7.17 (2H, d, J=7.12 Hz) 3.92 (1H, s) 3.23-3.29 (2H, m) 1.02 (6H, d, J=18.31 Hz).

Example 3

Ethyl 2,2-dimethyl-3-phenyl-3-(3-phenylH-imidazo[1,5-a]pyridin-7-yl)propylcarbamate

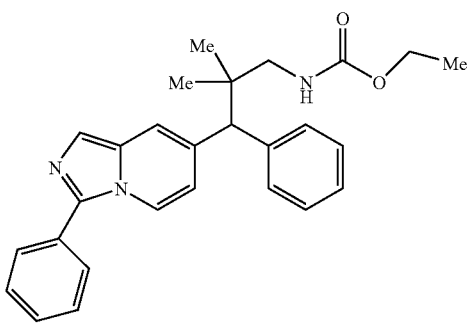

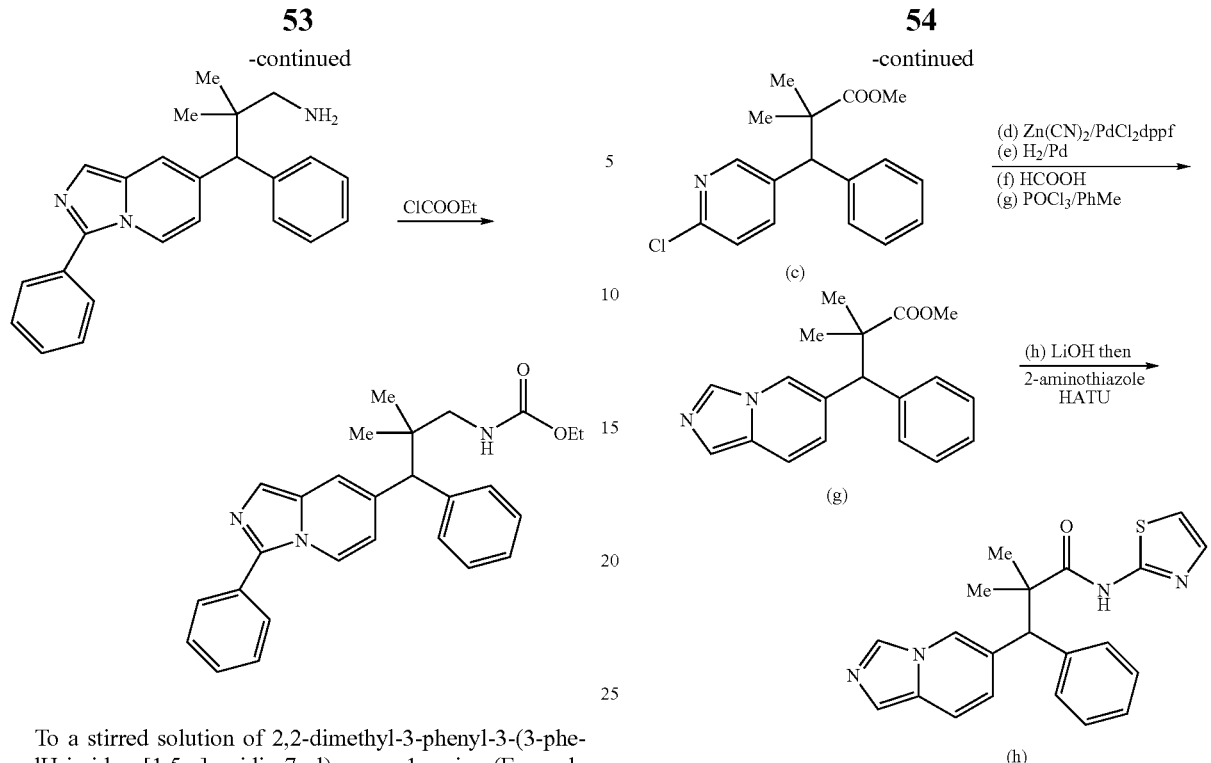

To a stirred solution of 2,2-dimethyl-3-phenyl-3-(3-phenyl1H-imidazo[1,5-a]pyridin-7-yl)propan-1-amine (Example 2(b), 15 mg, 0.042 mmol) and pyridine (0.1 mL) in anhydrous dichloromethane (1 mL) was added ethyl chloroformate (0.01 mL, 0.1 mmol) at rt under argon. The reaction mixture was stirred at room temperature for 45 minutes before saturated aqueous sodium bicarbonate solution (2 mL) was added to quench the reaction. The aqueous layer was separated and extracted with dichloromethane (2×2 mL). The combined dichloromethane solutions were dried ($Na_2SO_4$) and concentrated. Silica gel flash chromatography (0-100% ethyl acetate in hexanes) gave ethyl 2,2-dimethyl-3-phenyl-3-(3-phenyl1H-imidazo[1,5-a]pyridin-7-yl)propylcarbamate (5 mg, 0.012 mmol, 29% yield) as a solid. MS found: $(M+H)^+=428.35$. $^1$H NMR (400 MHz, $CDCl_3$) δ ppm 8.16 (1H, d, J=7.63 Hz) 7.75 (2H, d, J=7.12 Hz) 7.45-7.55 (4H, m) 7.36-7.44 (3H, m) 7.32 (2H, t, J=7.38 Hz) 7.21-7.26 (1H, m) 6.65 (1H, d, J=7.12 Hz) 4.60 (1H, s) 4.05-4.15 (2H, m) 3.75 (1H, s) 3.10-3.23 (2H, m) 1.18-1.28 (3H, m) 1.10 (6H, d, J=12.21 Hz).

Example 4

3-(H-Imidazo[1,5-a]pyridin-6-yl)-2,2-dimethyl-3-phenyl-N-(thiazol-2-yl)propanamide

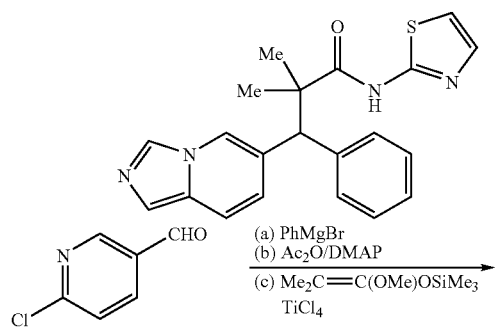

(a) To a stirred solution of 6-chloronicotinaldehyde (1.0 g, 7.1 mmol) in anhydrous tetrahydrofuran (10 mL) was added phenylmagnesium bromide solution (3M in diethyl ether, 2.6 mL, 7.8 mmol) dropwise at −78° C. under argon. After the reaction mixture was stirred at −78° C. for 10 min and 0° C. for 20 min, saturated aqueous ammonium chloride solution (10 mL) was added to quench the reaction. The mixture was extracted with ethyl acetate (3×10 mL). The combined ethyl acetate extracts were dried ($Na_2SO_4$) and concentrated to give (6-chloropyridin-3-yl)(phenyl)methanol (1.5 g, 6.8 mmol, 96% yield) as a yellow liquid. MS found: $(M+H)^+=220.09$.

(b) To a stirred solution of (6-chloropyridin-3-yl)(phenyl)methanol (1.5 g, 6.8 mmol), diisopropylethylamine (2.5 mL, 15 mmol), 4-dimethylaminopyridine (86 mg, 0.7 mmol) in anhydrous dichloromethane (4 mL) was added acetic anhydride (1.4 mL, 15 mmol) dropwise at 0° C. under argon. After the reaction mixture was stirred at room temperature for 2 hours, water (1 mL) and then saturated aqueous sodium bicarbonate solution (20 mL) were added slowly to quench the reaction. The mixture was stirred at room temperature for 30 minutes and then extracted with dichloromethane (3×10 mL). The combined dichlormethane extracts were dried ($Na_2SO_4$) and concentrated. Silica gel flash chromatography (0-100% ethyl acetate in hexanes) gave (6-chloropyridin-3-yl)(phenyl)methyl acetate (1.7 g, 6.5 mmol, 96% yield) as a colorless liquid. MS found: $(M+H)^+=262.13$.

(c) To a stirred solution of (6-chloropyridin-3-yl)(phenyl)methyl acetate (0.52 g, 2.0 mmol) and (1-methoxy-2-methylprop-1-enyloxy)trimethylsilane (2.0 mL, 9.8 mmol) in anhydrous dichloromethane (10 mL) was added titanium tetrachloride solution (1M in toluene, 4.4 mL, 4.4 mmol) dropwise at 0° C. under argon. After stirring at 0° C. for 48 hrs (refrigerator) and room temperature for 5 hours, the mixture was poured into a saturated aqueous sodium bicarbonate solution (40 mL) maintained at 0° C. The mixture was extracted with ethyl acetate (2×40 mL). The combined organic solutions were dried ($Na_2SO_4$) and concentrated. Silica gel flash chromatography (0-100% ethyl acetate in hexanes) gave methyl 3-(6-chloropyridin-3-yl)-2,2-dimethyl-3-phenylpropanoate (0.48 g, 1.6 mmol, 80% yield) as a colorless liquid. MS found: (M+H)+=304.25.

(d) A mixture of methyl 3-(6-chloropyridin-3-yl)-2,2-dimethyl-3-phenylpropanoate (0.11 g, 0.38 mmol), zinc cyanide (45 mg, 0.38 mmol), zinc (5 mg, 0.08 mmol), [1,1'-bis(diphenylphosphino)ferrocene]dichloropalladium(II) complex with dichloromethane (14 mg, 0.019 mmol), and N,N-dimethylacetamide (0.5 mL) was stirred at 120° C. under argon for 2 hr. The reaction mixture was concentrated under reduced pressure and the residue was partitioned between saturated aqueous sodium bicarbonate solution (10 mL) and ethyl acetate (20 mL). The aqueous layer was separated and extracted with ethyl acetate (10 mL). The combined organic solutions were dried (Na$_2$SO$_4$) and concentrated. Silica gel flash chromatography (0-100% ethyl acetate in hexanes) gave methyl 3-(6-cyanopyridin-3-yl)-2,2-dimethyl-3-phenylpropanoate (70 mg, 0.24 mmol, 63% yield) as a colorless solid. MS found: (M+H)+=295.27.

(e) A mixture of methyl 3-(6-cyanopyridin-3-yl)-2,2-dimethyl-3-phenylpropanoate (0.24 g, 0.81 mmol), palladium (10% on carbon, 93 mg), concentrated hydrochloric acid (0.19 mL), and methanol (7 mL) was stirred under hydrogen (balloon) for 2.5 hr. The mixture was then filtered. The filtrate was concentrated to remove methanol. The residue was made basic with saturated aqueous sodium bicarbonate solution (10 mL) and extracted with ethyl acetate (4×10 mL). The combined ethyl acetate extracts were washed with brine (5 mL), dried (Na$_2$SO$_4$) and concentrated to give methyl 3-(6-(aminomethyl)pyridin-3-yl)-2,2-dimethyl-3-phenylpropanoate (0.24 g, 0.80 mmol, 99% yield) as a solid. MS found: (M+H)+=299.31.

(f) To a stirred solution of methyl 3-(6-(aminomethyl)pyridin-3-yl)-2,2-dimethyl-3-phenylpropanoate (0.24 g, 0.80 mmol) in formic acid (3 mL) was added potassium carbonate (0.2 g) portionwise. The reaction mixture was stirred at 90° C. overnight under argon and then concentrated. The residue was made basic with saturated aqueous sodium bicarbonate solution (20 mL) and extracted with dichloromethane (3×20 mL). The combined dichloromethane extracts were dried (Na$_2$SO$_4$) and concentrated. Silica gel flash chromatography (20-100% ethyl acetate in hexanes) gave methyl 3-(6-(formamidomethyl)pyridin-3-yl)-2,2-dimethyl-3-phenylpropanoate (0.19 g, 0.58 mmol, 73% yield) as a solid. MS found: (M+H)+=327.35.

(g) A mixture of methyl 3-(6-(formamidomethyl)pyridin-3-yl)-2,2-dimethyl-3-phenylpropanoate (0.19 g, 0.58 mmol), anhydrous toluene (3 mL), and phosphorus oxychloride (0.11 mL, 1.2 mmol) was stirred at 115° C. for 2.5 hr under slow argon stream. The mixture was then made basic with saturated aqueous sodium bicarbonate solution (10 mL) and potassium carbonate (0.5 g). The aqueous layer was separated and extracted with dichloromethane (2×10 mL). The combined organic solutions were dried (Na$_2$SO$_4$) and concentrated. Silica gel flash chromatography (0-100% ethyl acetate in hexanes) gave methyl 3-(H-imidazo[1,5-a]pyridin-6-yl)-2,2-dimethyl-3-phenylpropanoate (0.17 g, 0.55 mmol, 95% yield) as a solid. MS found: (M+H)+=309.35.

(h) Methyl 3-(H-imidazo[1,5-a]pyridin-6-yl)-2,2-dimethyl-3-phenylpropanoate was converted to 3-(H-imidazo[1,5-a]pyridin-6-yl)-2,2-dimethyl-3-phenyl-N-(thiazol-2-yl)propanamide as a TFA salt using procedures outlined for Example 1(g), 1(h). MS found: (M+H)+=377.36. $^1$H-NMR (400 MHz, MeOD): δ ppm 9.30 (1H, s) 8.51 (1H, s) 7.79 (1H, s) 7.56 (1H, d, J=9.66 Hz) 7.29-7.35 (3 H, m) 7.15-7.26 (3H, m) 7.08 (1H, d, J=8.65 Hz) 6.97 (1H, d, J=3.56 Hz) 4.55 (1H, s) 1.37 (6H, d, J=18.82 Hz).

Example 5

3-(1-(4-Fluorophenyl)H-imidazo[1,5-a]pyridin-6-yl)-2,2-dimethyl-3-phenyl-N-(thiazol-2-yl)propanamide

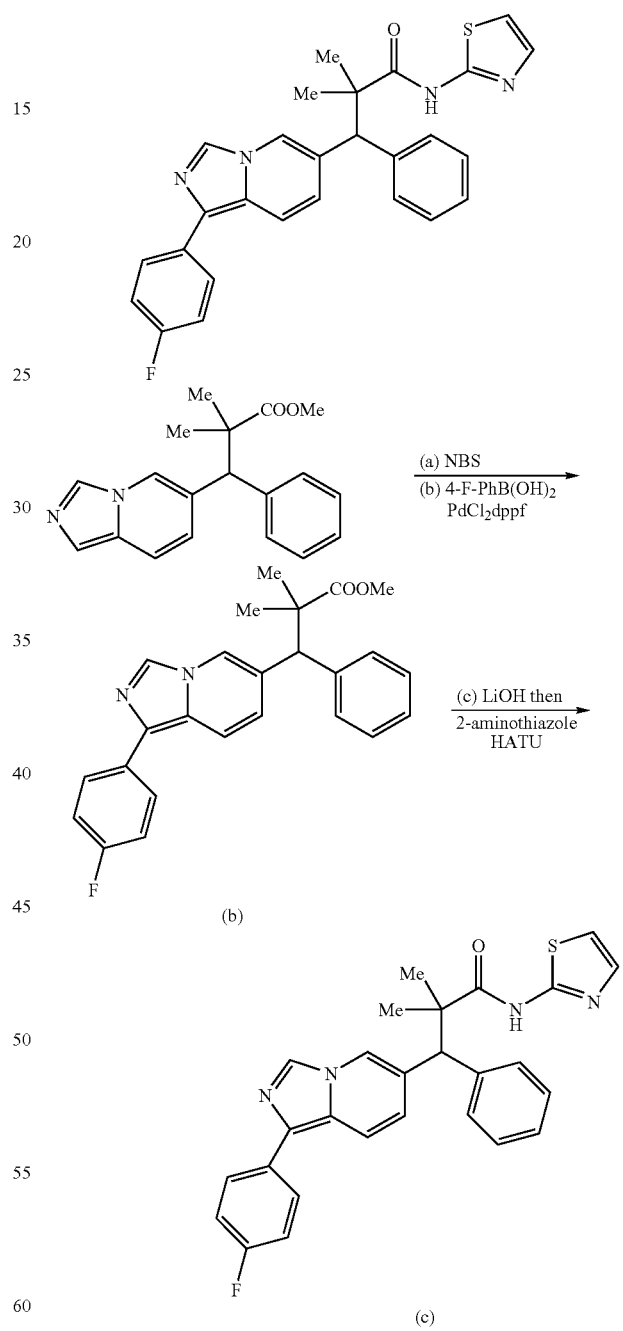

(a) To a stirred solution of methyl 3-(H-imidazo[1,5-a]pyridin-6-yl)-2,2-dimethyl-3-phenylpropanoate (Example 4(g), 67 mg, 0.22 mmol) in anhydrous acetonitrile (4 mL) cooled in an ice-sodium chloride bath was added NBS (39 mg, 0.22 mmol). The reaction mixture was stirred at 0° C. for 15 minutes, and at room temperature for 15 minutes before diisopropylethylamine (0.4 mL) was added. The mixture was concentrated under reduced pressure. Silica gel flash chromatography (0-100% ethyl acetate in hexanes) gave methyl 3-(1-bromoH-imidazo[1,5-a]pyridin-6-yl)-2,2-dimethyl-3-phenylpropanoate (48 mg, 0.12 mmol, 56% yield) as a solid. MS found: $(M+H)^+=387.24$ and 389.25.

(b) A mixture of methyl 3-(1-bromoH-imidazo[1,5-a]pyridin-6-yl)-2,2-dimethyl-3-phenylpropanoate (48 mg, 0.12 mmol), 4-fluorophenylboronic acid (34 mg, 0.24 mmol), [1,1'-bis(diphenylphosphino)ferrocene]dichloropalladium (II) complex with dichloromethane (4 mg, 0.006 mmol), aqueous potassium phosphate solution (2M, 0.24 mL, 0.48 mmol), and DMF (1 mL) was degassed and then stirred at 80° C. for 2 hr under argon. The reaction mixture was concentrated under reduced pressure. The residue was mixed with saturated aqueous sodium bicarbonate solution (5 mL) and extracted with dichloromethane (3×5 mL). The combined dichloromethane extracts were dried ($Na_2SO_4$) and concentrated. Silica gel flash chromatography (0-100% ethyl acetate in hexanes) gave methyl 3-(1-(4-fluorophenyl)H-imidazo[1,5-a]pyridin-6-yl)-2,2-dimethyl-3-phenylpropanoate (42 g, 0.10 mmol, 87% yield) as a solid. MS found: $(M+H)^+=403.35$.

(c) Methyl 3-(1-(4-fluorophenyl)H-imidazo[1,5-a]pyridin-6-yl)-2,2-dimethyl-3-phenylpropanoate was converted to 3-(1-(4-fluorophenyl)H-imidazo[1,5-a]pyridin-6-yl)-2,2-dimethyl-3-phenyl-N-(thiazol-2-yl)propanamide as a TFA salt using procedures outlined for Example 1(g), 1(h). MS found: $(M+H)^+=471.31$. $^1H$ NMR (500 MHz, MeOD) δ ppm 9.04 (1H, s) 8.49 (1H, s) 7.73-7.77 (3H, m) 7.42 (2H, d, J=7.70 Hz) 7.40 (1H, d, J=3.30 Hz) 7.32 (2H, t, J=7.70 Hz) 7.26 (3H, t, J=8.52 Hz) 7.08 (1H, d, J=9.90 Hz) 7.06 (1H, d, J=3.85 Hz) 4.61 (1H, s) 1.46 (6H, d, J=21.44 Hz).

Example 6

3-(1-BromoH-imidazo[1,5-a]pyridin-6-yl)-2,2-dimethyl-3-phenyl-N-(thiazol-2-yl)propanamide

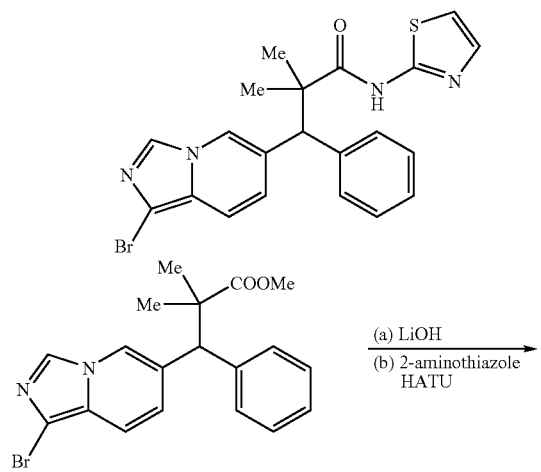

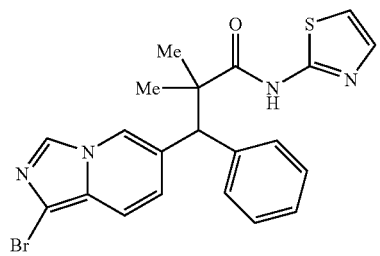

(a) Methyl 3-(1-bromoH-imidazo[1,5-a]pyridin-6-yl)-2,2-dimethyl-3-phenylpropanoate (Example 5(a)) was converted to 3-(1-bromoH-imidazo[1,5-a]pyridin-6-yl)-2,2-dimethyl-3-phenylpropanoic acid using the procedure outlined for Example 1(g).

(b) 3-(1-bromoH-imidazo[1,5-a]pyridin-6-yl)-2,2-dimethyl-3-phenylpropanoic acid was converted to 3-(1-bromoH-imidazo[1,5-a]pyridin-6-yl)-2,2-dimethyl-3-phenyl-N-(thiazol-2-yl)propanamide as a TFA salt using the procedure outlined for Example 1(h). MS found: $(M+H)^+=455.22$. $^1H$ NMR (500 MHz, $CDCl_3$) δ ppm 8.81 (1H, s) 7.98 (1H, s) 7.97 (1H, s) 7.42 (1H, d, J=3.85 Hz) 7.22-7.32 (4H, m) 7.09 (1H, d, J=3.85 Hz) 6.98 (1H, d, J=3.85 Hz) 6.75 (1H, d, J=8.25 Hz) 6.55 (1H, d, J=3.85 Hz) 4.31 (1H, s) 1.46 (6H, d, J=21.99 Hz).

Example 7

3-(1-(3-Cyanophenyl)H-imidazo[1,5-a]pyridin-6-yl)-2,2-dimethyl-3-phenyl-N-(thiazol-2-yl)propanamide

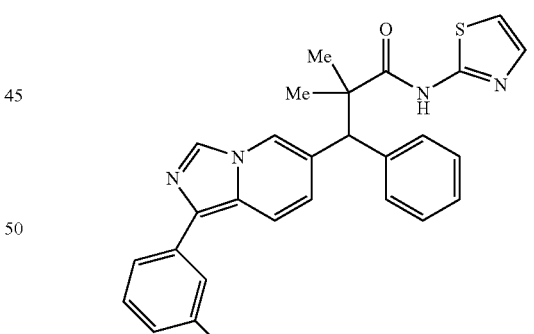

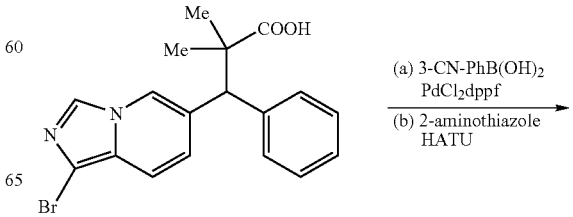

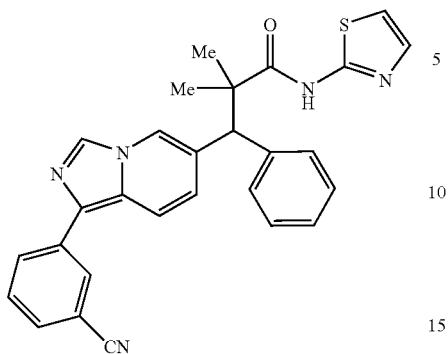

(a) 3-(1-BromoH-imidazo[1,5-a]pyridin-6-yl)-2,2-dimethyl-3-phenylpropanoic acid (Example 6(a)) was converted to 3-(1-(3-cyanophenyl)H-imidazo[1,5-a]pyridin-6-yl)-2,2-dimethyl-3-phenylpropanoic acid using the procedure outlined for Example 5(b).

(b) 3-(1-(3-cyanophenyl)H-imidazo[1,5-a]pyridin-6-yl)-2,2-dimethyl-3-phenylpropanoic acid was converted to 3-(1-(3-cyanophenyl)H-imidazo[1,5-a]pyridin-6-yl)-2,2-dimethyl-3-phenyl-N-(thiazol-2-yl)propanamide as a TFA salt using the procedure outlined for Example 1(h). MS found: $(M+H)^+=478.21$. $^1$H NMR (400 MHz, MeOD) δ ppm 9.00 (1H, s) 8.54 (1H, s) 8.12 (1H, s) 8.07 (1H, d, J=7.63 Hz) 7.85 (1H, d, J=10.17 Hz) 7.66-7.77 (2H, m) 7.41-7.48 (3H, m) 7.35 (2H, t, J=7.12 Hz) 7.28 (1H, t, J=7.12 Hz) 7.16 (1H, d, J=9.66 Hz) 7.09 (1H, d, J=3.56 Hz) 4.65 (1H, s) 1.49 (6H, d, J=17.29 Hz).

Example 8

3-([1,2,4]-Triazolo[4,3-a]pyridin-6-yl)-2,2-dimethyl-3-phenyl-N-(thiazol-2-yl)propanamide

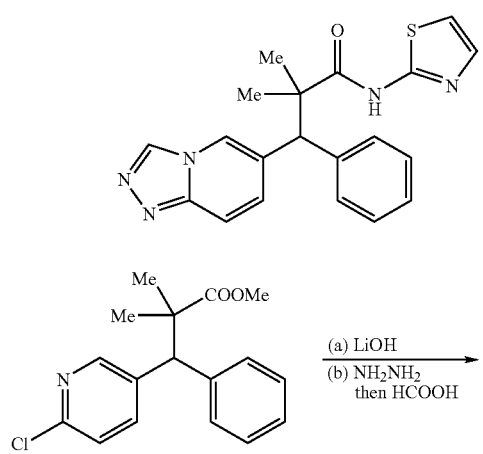

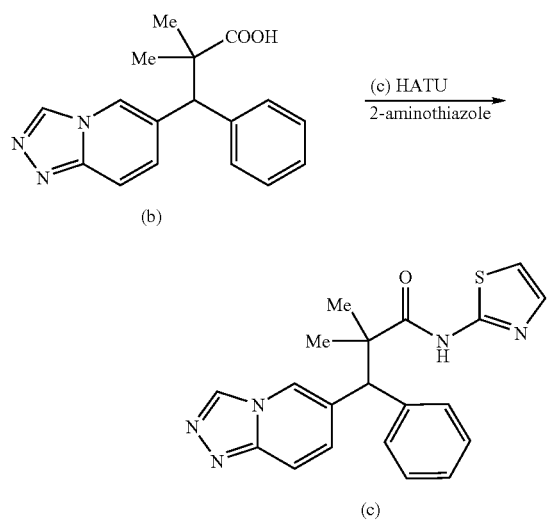

(a) A mixture of methyl 3-(6-chloropyridin-3-yl)-2,2-dimethyl-3-phenylpropanoate (Example 4(c), 67 mg, 0.22 mmol), lithium hydroxide monohydrate (55 mg, 1.3 mmol), water (2 mL), and dioxane (2 mL) was stirred at 110° C. for 1.5 hr and then concentrated. The residue was partitioned between water (4 mL) and diethyl ether (6 mL) were added. The ether layer was reextracted with water (1 mL). The combined aqueous solutions were neutralized with aqueous 10% citric acid solution to pH=5 and extracted with ethyl acetate (3×5 mL). The combined ethyl acetate extracts were washed with brine (2 mL), dried ($Na_2SO_4$) and concentrated to give 3-(6-chloropyridin-3-yl)-2,2-dimethyl-3-phenylpropanoic acid (57 mg, 0.20 mmol, 89% yield). MS found: $(M-H)^-=288.19$.

(b) A mixture of 3-(6-chloropyridin-3-yl)-2,2-dimethyl-3-phenylpropanoic acid (28 mg, 0.10 mmol), potassium carbonate (8 mg), and hydrazine (0.5 mL) was stirred at 110° C. for 11 hr under argon and then concentrated. The residue was mixed with formic acid (1 mL). The mixture was stirred at 100° C. for 2 hr and 120° C. for 1 hr. Concentration and purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 3-([1,2,4]triazolo[4,3-a]pyridin-6-yl)-2,2-dimethyl-3-phenylpropanoic acid (33 mg, 0.081 mmol, 81% yield) as a TFA salt. MS found: $(M+H)^+=296.25$.

(c) 3-([1,2,4]triazolo[4,3-a]pyridin-6-yl)-2,2-dimethyl-3-phenylpropanoic acid was converted to 3-([1,2,4]triazolo[4,3-a]pyridin-6-yl)-2,2-dimethyl-3-phenyl-N-(thiazol-2-yl)propanamide using the procedure outlined for Example 1(h). MS found: $(M+H)^+=378.27$. $^1$H NMR (400 MHz, MeOD) δ ppm 9.24 (1H, s) 8.77 (1H, s) 7.77-7.82 (1H, m) 7.70-7.75 (1H, m) 7.33 (1H, s) 7.32 (2H, d, J=3.56 Hz) 7.23 (2H, t, J=7.38 Hz) 7.18 (1H, d, J=7.12 Hz) 6.98 (1H, d, J=3.56 Hz) 4.64 (1H, s) 1.37 (6H, d, J=19.33 Hz).

Examples 9 to 26

Compounds in Table 1 (below) were synthesized using the protocols outlined above.

TABLE 1

| Example No. | Structure | LC Retention Time (Min.) /Column* | LC-MS [M + H]+ | Procedure of Example |
|---|---|---|---|---|
| 9 | 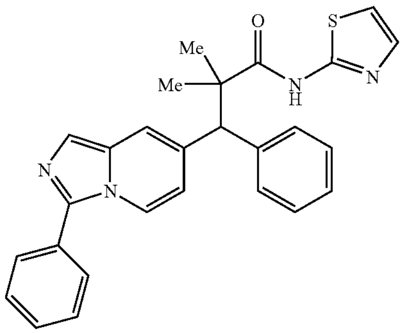 | 2.74/A | 453.23 | 1 |
| 10 | 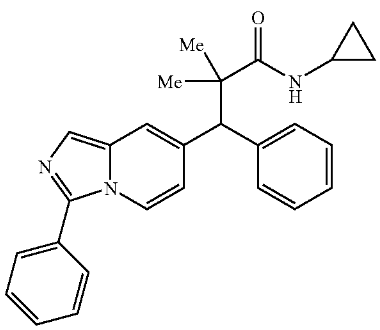 | 2.47/A | 410.36 | 1 |
| 11 | 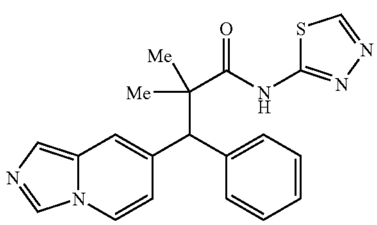 | 2.04/A | 378.24 | 1 |
| 12 | 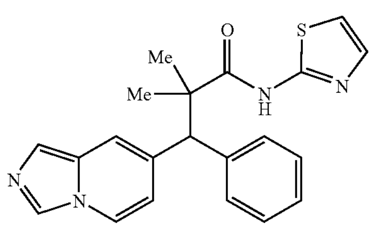 | 2.29/B | 377.25 | 1 |
| 13 | 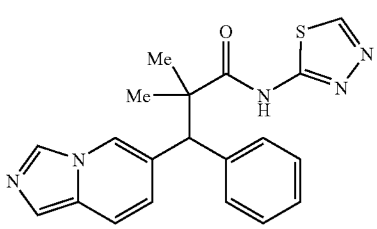 | 2.08/A | 378.33 | 4 |

TABLE 1-continued

| Example No. | Structure | LC Retention Time (Min.) /Column* | LC-MS [M + H]+ | Procedure of Example |
|---|---|---|---|---|
| 14 | 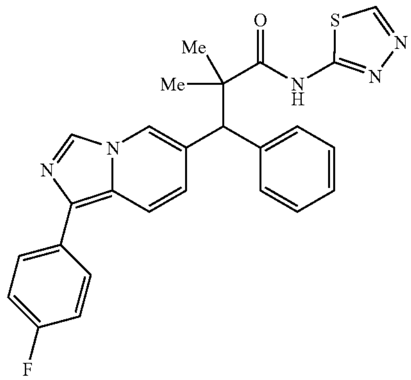 | 3.30/A | 472.28 | 5 |
| 15 | 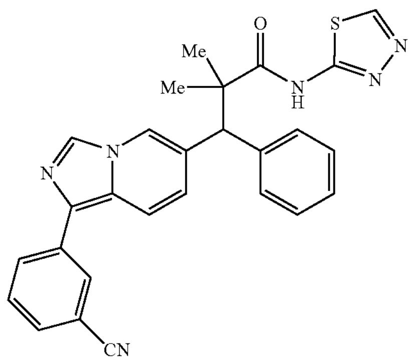 | 3.55/A | 479.19 | 7 |
| 16 | 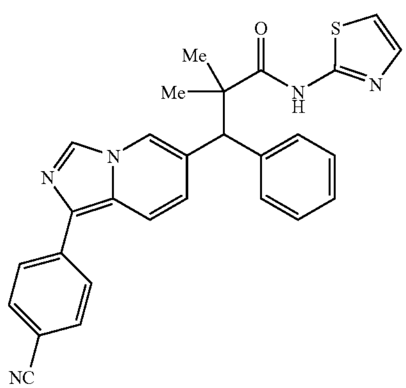 | 3.70/A | 478.21 | 7 |
| 17 | 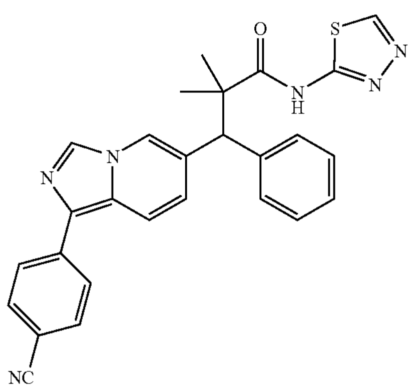 | 3.53/A | 479.22 | 7 |

TABLE 1-continued

| Example No. | Structure | LC Retention Time (Min.) /Column* | LC-MS [M + H]+ | Procedure of Example |
|---|---|---|---|---|
| 18 | 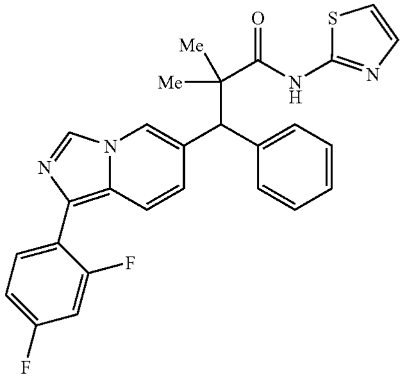 | 3.76/A | 489.20 | 7 |
| 19 | 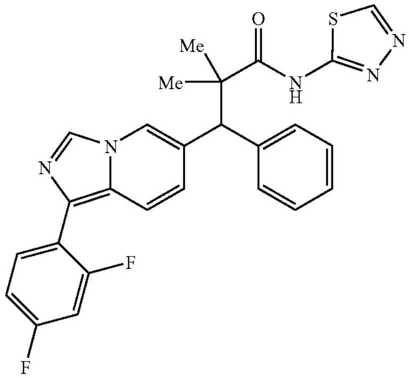 | 3.63/A | 490.22 | 7 |
| 20 | 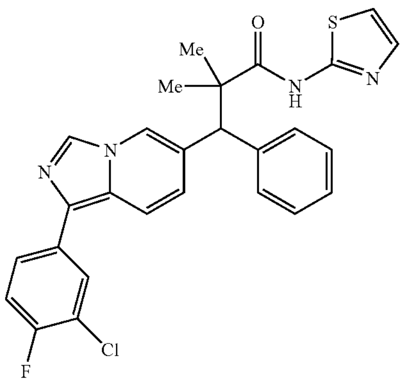 | 4.05/A | 505.16 | 7 |
| 21 | 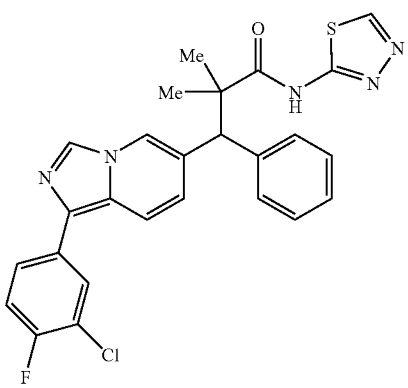 | 3.92/A | 506.17 | 7 |

TABLE 1-continued

| Example No. | Structure | LC Retention Time (Min.) /Column* | LC-MS [M + H]+ | Procedure of Example |
| --- | --- | --- | --- | --- |
| 22 | 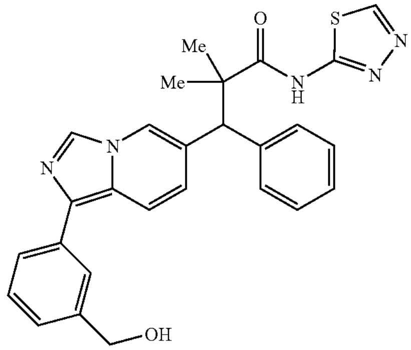 | 2.89/A | 484.17 | 7 |
| 23 | 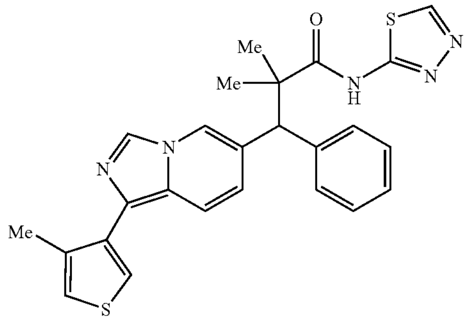 | 3.17/A | 474.13 | 7 |
| 24 | 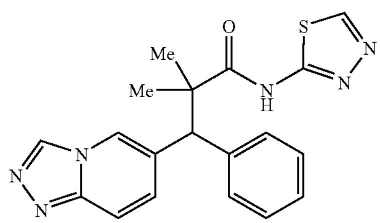 | 2.21/A | 379.27 | 8 |
| 25 | 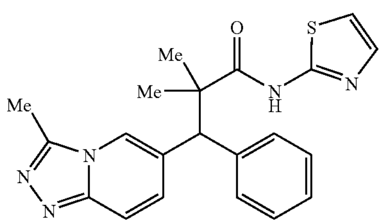 | 2.41/A | 392.29 | 8 |
| 26 | 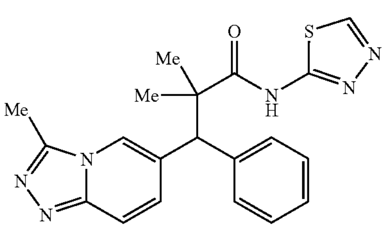 | 2.13/A | 393.22 | 8 |

*HPLC conditions:
Column:
A: YMC S5 CombiScreen column 4.6 × 50 mm
B: YMC S5 ODS column 4.6 × 50 mm
Solvents: 10-90% aqueous methanol over 4 minutes containing 0.2% phosphoric acid,
Flow rate: 4 mL/min,
Detection: UV at 220 nm.

Biological Activity Data

The AP-1 activity of Examples 1 to 26 is given where the AP-1 EC$_{50}$ is less than 1 uM. Accompanying AP-1 maximum inhibition values are also given. Where the AP-1 EC50 is greater than 1 uM and/or the maximal inhibition is less than 20%, the glucocorticoid receptor (GR) binding affinity (Ki) is given.

The data presented below were obtained using the assays referred to in the table and described herein in the ASSAY section supra.

| Example No. | GR (Ki, nM) (GR Binding Assay) | AP-1 EC$_{50}$, nM (Cellular Transrepression Assay) | AP-1 Max % inh (Cellular Transrepression Assay) |
|---|---|---|---|
| 1 |  | 112.10 | 63.58 |
| 2 | 16.50 |  |  |
| 3 | 27.40 |  |  |
| 4 | 13.00 |  |  |
| 5 |  | 34.12 | 71.08 |
| 6 | 30.20 |  |  |
| 7 | 17.00 |  |  |
| 8 | 169.40 |  |  |
| 9 |  | 10.09 | 67.35 |
| 10 | 7.30 |  |  |
| 11 | 27.10 |  |  |
| 12 | 17.70 |  |  |
| 13 | 19.50 |  |  |
| 14 |  | 43.59 | 55.80 |
| 15 | 22.60 |  |  |
| 16 | 26.20 |  |  |
| 17 | 20.00 |  |  |
| 18 |  | 12.96 | 55.81 |
| 19 |  | 16.01 | 45.65 |
| 20 | 65.90 |  |  |
| 21 | 46.60 |  |  |
| 22 | 12.20 |  |  |
| 23 | 36.00 |  |  |
| 24 | 327.00 |  |  |
| 25 | 2364.00 |  |  |
| 26 | 5455.00 |  |  |

What is claimed is:

1. A compound according to formula I,

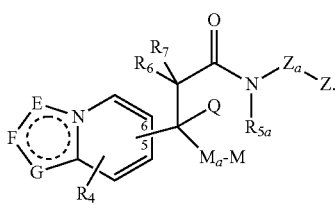

its enantiomer, diastereomers, and tautomers, or a pharmaceutically-acceptable salt, or hydrate, thereof, wherein the side chain group:

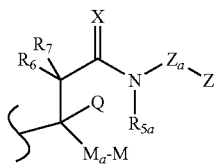

is attached to the benzo ring at the 5- or 6-position;

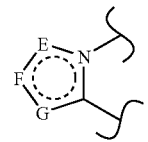

is heterocyclo or heteroaryl;
E is —CR$_2$—;
F is selected from —N— and —CR$_{2a}$—;
G is selected from N and —CR$_{2b}$—;
X is selected from O and (R$^x$)(R$^y$);
M is selected from hydrogen, alkyl, alkenyl, alkynyl, cycloalkyl, cycloalkenyl, aryl, heterocyclo, and heteroaryl;
M$_a$ is a linker between C and M and is selected from a bond; C$_1$-C$_5$ alkylene; C$_1$-C$_5$ alkylene which includes at any position in the chain a) a nitrogen which is substituted with alkyl, b) an oxygen, c) a sulfur, or d) an SO$_2$ group; —C(R$_{m^1}$)(R$_{m^2}$)C(=O)N(R$_{m^3}$)—; —C(=O)N(R$_{m^1}$)C(R$_{m^2}$)(R$_{m^3}$)—; —N(R$_{m^3}$)C(=O)C(R$_{m^1}$)(R$_{m^2}$)—; —C(R$_{m^1}$)(R$_{m^2}$)S(=O)$_2$N(R$_{m^3}$)—; —S(=O)$_2$N(R$_{m^1}$)C(R$_{m^2}$)(R$_{m^3}$)—; and —N(R$_{m^1}$)C(=O)N(R$_{m^2}$)—; (R$_m$ where R$_{m^1}$, R$_{m^2}$ and R$_{m^3}$ are the same or different and at each occurrence independently selected from H and C$_1$-C$_4$ alkyl, or R$_{m^1}$ and R$_{m^2}$ combine to form a C$_{3-6}$ carbocyclic or heterocyclo ring;
Q is selected from
   (i) hydrogen, halogen, nitro, cyano, hydroxy, unsubstituted C$_1$-C$_4$ alkyl, and substituted C$_1$-C$_4$ alkyl; or
   (ii) Q and R$_6$ are combined with the carbons to which they are attached to form a 3- to 6-membered cycloalkyl or heterocyclo ring;
   (iii) Q and M-M$_a$ are combined with the carbon to which they are attached to form a 3-7 membered ring optionally containing of 0, 1 or 2 heteroatoms which are the same or different and are independently selected form the group consisting of O, S, SO, SO$_2$, and N—R$_{5b}$, provided that the heterocyclic ring formed does not contain a S—S or S—O bond, wherein this ring may be optionally substituted with 0, 1 or 2 R$_3$ groups or carbonyl;
where X is O, Z is selected from
   (i) alkyl, cycloalkyl, heterocyclo, alkylsulfonyl, aryl, and heteroaryl; and
   (ii) Z is combined with R$_{5a}$ and to the carbon to which they are attached to form a 3-6 membered heterocyclic ring which is optionally substituted with 1-2 R$_3$ groups or carbonyl;
or when X=(R$^x$)(R$^y$), Z is selected from
   (i) alkyl, cycloalkyl, heterocyclo, aryl, heteroaryl, —C(=O)NR$_8$R$_9$, —C(=O)R$_8$, —C(NCN)NR$_8$R$_9$, C(=O)OR$_8$, —SO$_2$R$_8$, and —SO$_2$NR$_8$R$_9$; or
   (ii) Z is combined with R$_{5a}$ to form a 3-6 membered heterocyclic ring which is optionally substituted with 1-2 R$_3$ or carbonyl;
Z$_a$ is a linker between N and Z and is selected from a bond; C$_1$-C$_5$ alkylene; C$_1$-C$_5$ alkylene which includes at any position in the chain a) a nitrogen which is substituted with alkyl, b) an oxygen, c) a sulfur, or d) an SO$_2$ group; —C(R$_{z^1}$)(R$_{z^2}$)C(=O)N(R$_{z^3}$)—; —C(=O)N(R$_{z^1}$)C(R$_{z^2}$)(R$_{z^3}$)—; —C(R$_{z^1}$)(R$_{z^2}$)S(=O)$_2$N(R$_{z^3}$)—; and —S(=O)₂ N(R$_{z^1}$)C(R$_{z^2}$)(R$_{z^3}$)—; where R$_{z^1}$, R$_{z^2}$ and R$_{z^3}$ at each occurrence are independently selected from H and C$_1$-C$_4$ alkyl;

R$_1$, R$_{1a}$, R$_{1b}$, R$^x$ and R$^y$ are the same or different and at each occurrence are independently selected from hydrogen, alkyl, alkenyl, alkynyl, cycloalkyl, cycloalkenyl, aryl, heteroaryl, and heterocyclo;

R$_2$, R$_{2a}$ and R$_{2b}$ are the same or different and at each occurrence are independently selected from
(i) hydrogen, halogen, alkyl, alkenyl, alkynyl, nitro, cyano, —OR$_{10}$, —NR$_{10}$R$_{11}$, —C(=O)R$_{10}$, —CO$_2$R$_{10}$, —C(=O)NR$_{10}$R$_{11}$, —O—C(=O)R$_{10}$, —NR$_{10}$C(=O)R$_{11}$, —NR$_{10}$C(O)OR$_{11}$, —NR$_{10}$C(S)OR$_{11}$, —S(O)$_p$R$_{12}$, —NR$_8$SO$_2$R$_{12}$, —SO$_2$NR$_{10}$R$_{11}$, cycloalkyl, cycloalkenyl, cycloalkynyl, heterocyclo, aryl, and heteroaryl; or
(ii) two R$_2$, R$_{2a}$ and R$_{2b}$ groups that are located on adjacent carbon atoms may be taken together with the carbons to which they are attached to form a fused ring;

R$_3$ at each occurrence is independently selected from hydrogen, halogen, alkyl, alkenyl, alkynyl, cyano, —OR$_{13}$, —NR$_{13}$R$_{14}$, —C(=O)R$_{13}$, —CO$_2$R$_{13}$, —C(=O)NR$_{13}$R$_{14}$, —O—C(=O)R$_{13}$, —NR$_{13}$C(=O)R$_{14}$, —NR$_{13}$C(O)OR$_{14}$, —NR$_{13}$C(S)OR$_{14}$, —S(O)$_p$R$_{15}$, —NR$_{13}$SO$_2$R$_{15}$, —SO$_2$NR$_{13}$R$_{14}$, cycloalkyl, cycloalkenyl, cycloalkynyl, heterocyclo, aryl, and heteroaryl;

R$_4$ is selected from hydrogen, halogen, alkyl, alkenyl, alkynyl, cyano, and C$_1$-C$_4$ alkoxy;

R$_{5a}$ is selected from hydrogen and alkyl; and

R$_6$ is selected from hydrogen, halogen, alkyl, alkenyl, alkynyl, nitro, cyano, —OR$_{16}$, —NR$_{16}$R$_{17}$, —C(=O)R$_{17}$, —CO$_2$R$_{17}$, —C(=O)NR$_{16}$R$_{17}$, —O—C(=O)R$_{16}$, —NR$_{16}$C(=O)R$_{17}$, —NR$_{16}$C(=O)OR$_{17}$, —NR$_{16}$C(=S)OR$_{17}$, —S(O)$_p$R$_{18}$, —NR$_{16}$SO$_2$R$_{18}$, —SO$_2$NR$_{16}$R$_{17}$, cycloalkyl, cycloalkenyl, heterocyclo, aryl, and heteroaryl;

R$_7$ is selected from hydrogen, halogen, alkyl, alkenyl, alkynyl, nitro, cyano, OR$_{19}$, NR$_{19}$R$_{20}$, —C(=O)R$_{19}$, —CO$_2$R$_{19}$, —C(=O)NR$_{19}$R$_{20}$, —O—C(=O)R$_{19}$, —NR$_{19}$C(=O)R$_{20}$, —NR$_{19}$C(=O)OR$_{20}$, —NR$_{19}$C(=S)OR$_{20}$, —S(O)$_p$R$_{21}$, —NR$_{19}$SO$_2$R$_{21}$, —SO$_2$NR$_{19}$R$_{20}$, cycloalkyl, cycloalkenyl, cycloalkynyl, heterocyclo, aryl, and heteroaryl;

or R$_6$ and R$_7$ are taken together with the carbon to which they are attached to form a cycloalkyl, cycloalkenyl, or heterocyclo ring;

R$_{5b}$, R$_8$, R$_9$, R$_{10}$, R$_{11}$, R$_{13}$, R$_{13a}$, R$_{14}$, R$_{16}$, R$_{17}$, R$_{19}$ and R$_{20}$ are the same or different and at each occurrence are independently selected from
(i) hydrogen, alkyl, alkenyl, alkynyl, cycloalkyl, cycloalkenyl, aryl, heteroaryl, and heterocyclo; or
(ii) with respect to Z, R$_8$ taken together with R$_9$, and/or with respect to R$_3$ and R$_6$, R$_{15}$ is taken together with R$_{16}$, and/or with respect to R$_6$ and R$_7$, R$_{18}$ is taken together with R$_{19}$, and/or with respect to R$_7$, R$_{20}$ is taken together with R$_{21}$ to form a 4- to 6-membered heteroaryl or heterocyclo ring;

R$_{12}$, R$_{15}$, R$_{18}$ and R$_{21}$ are the same or different and are independently selected from alkyl, alkenyl, alkynyl, cycloalkyl, cycloalkenyl, aryl, heteroaryl, and heterocyclo; and p is 0, 1 or 2, provided that where the ring system

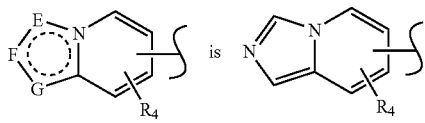

is and Q and M$_a$-M are independently H, CH$_3$ or C$_2$H$_5$, then Z$_a$—Z is other than

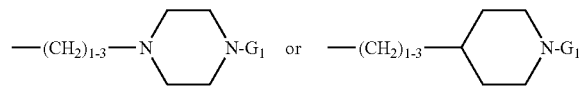

where G$_1$ is a heteroaryl, acetyl, carbamoyl, or —C(=S)CH$_3$ or —C(=S)C$_2$H$_5$.

2. The compound according to claim 1 having the structure

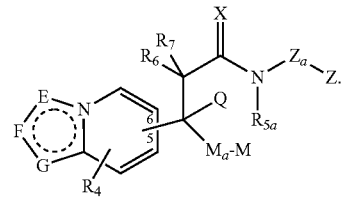

3. The compound according to claim 1 having the structure

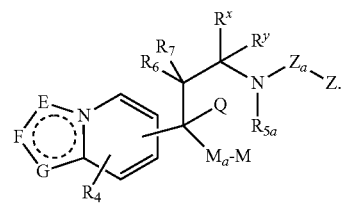

4. The compound as defined in claim 1 where in

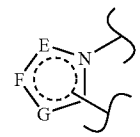

E is CR$_2$;
F is N; and
G is CR$_{2b}$;
X is (R$^x$)(R$^y$) where R$^x$ and R$^y$ are the same or different and are independently selected from H and alkyl; or
X is O;
R$_6$ is alkyl or H;
R$_7$ is alkyl or H;
M is aryl or H;
M$_a$ is a bond;
Q is H; or
E is CR$_2$ where R$_2$ is H, aryl or alkyl;
F is N or CR$_{2a}$;
G is CR$_{2b}$ where $R_{2b}$ is selected from haloaryl, halo, cyanoaryl, H, dihaloaryl, hydroxyalkylaryl and heteroaryl, or G is N;

where X is $(R^x)(R^y)$ then Z is selected from cycloalkyl, heteroaryl, aryl, heterocyclo, —C(=O)NR$_8$R$_9$, —C(=O)R$_8$, —C(NCN)NR$_8$R$_9$, and —C(=O)OR$_8$;

where X is O then Z is selected from heteroaryl, cycloalkyl, aryl, heterocyclo, and alkyl; and $Z_a$ is a bond.

5. The compound as defined in claim 1 wherein

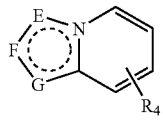

is selected from

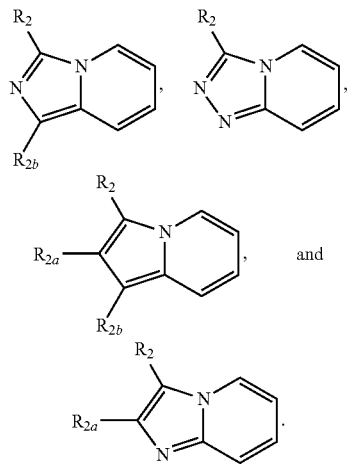

6. The compound as defined in claim 1 wherein

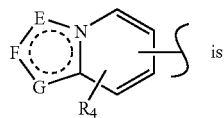 is a) 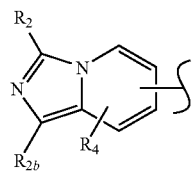

where $R_2$ is selected from aryl, H and alkyl,
$R_{2b}$ is selected from H, halogen, aryl, and heteroaryl;
and $R_4$ is selected from H and methyl; or b) 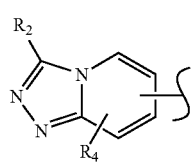

where $R_2$ is selected from H, alkyl and aryl;
and $R_4$ is selected from H and methyl.

7. A compound as defined in claim 1 wherein:
Z is selected from

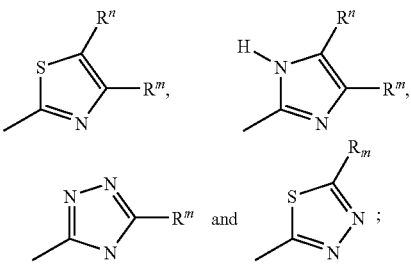

$R^m$ and $R^n$ are the same or different and at each occurrence are independently selected from hydrogen, halogen, cycloalkyl, cyano, —CO$_2$R$^c$, —NR$^a$R$^b$, —C(=O)R$^c$, —C(O)N(R$^a$)(R$^b$), OR$^c$, alkyl, substituted alkyl, aryl, heteroaryl and heterocyclo;

or $R^m$ and $R^n$ combine to form a 5-, 6- or 7-membered carbocyclic, aryl, heteroaryl or cycloheteroalkyl ring which contains 0, 1, 2 or 3 hetero atoms which can be N, O, or S;

$R^a$ and $R^b$ are the same or different and at each occurrence are independently selected from (1) hydrogen, alkyl, C(=O)alkyl, CO$_2$(alkyl), SO$_2$alkyl, alkenyl, alkynyl, amino, aryl, heteroaryl, cycloalkenyl, heterocyclo, and cycloalkyl, provided $R^a$ and $R^b$ are not both alkoxy, amino, or substituted amino, or (2) where possible $R^a$ is taken together with $R^b$ to form a heteroaryl or heterocyclo ring; and $R^c$ is selected from hydrogen, alkyl, alkenyl, alkynyl, alkoxy, amino, heteroaryl, heterocyclo, cycloalkyl, and aryl.

8. The compound as defined in claim 4 wherein G is N or G is CR$_{2b}$ and $R_{2b}$ is

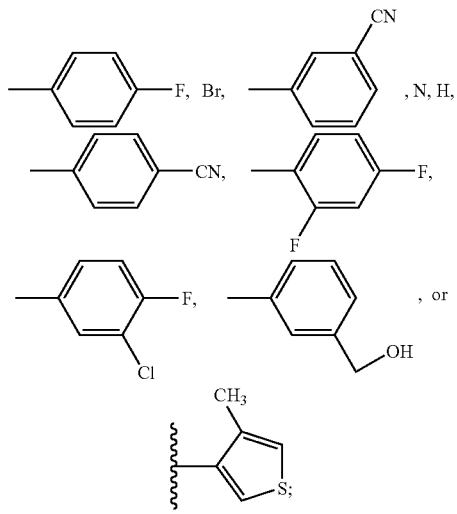

E is CR$_2$ and $R_2$ is

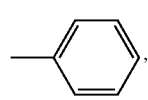

H or CH$_3$;
F is N; and
$R_6$ is CH$_3$ or H;

$R_7$ is $CH_3$ or H; and

M-$M_a$ is

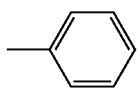

or H.

9. The compound as defined in claim 5 wherein Z is

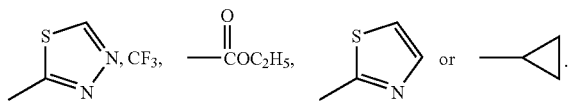

10. The compound as defined in claim 1 wherein

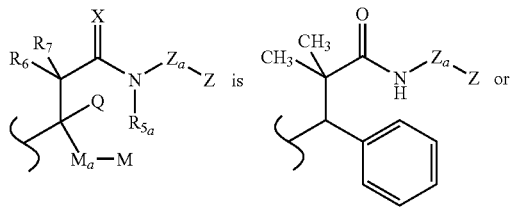

is

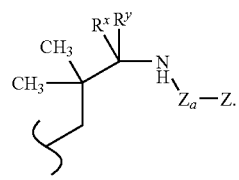

11. The compound as defined in claim 1 having the structure

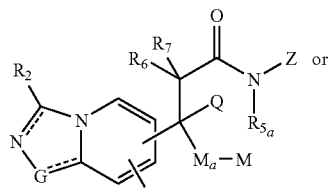

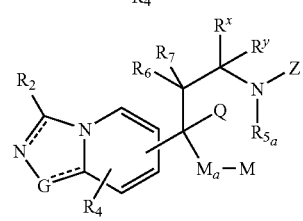

where

G is N or $CR_{2b}$;

$R_2$ is H, $CH_3$ or

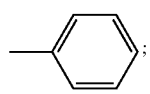

$R_{2b}$ is Br,

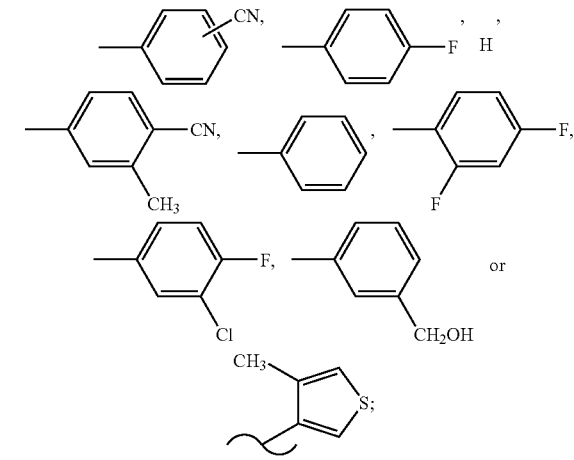

$R_4$ is H or $CH_3$;
$R_6$ is H or $CH_3$;
$R_7$ is H or $CH_3$;
Q is

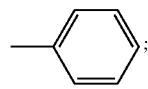

M is H;
$M_a$ is a bond;
$R_{5a}$ is H;
Z is

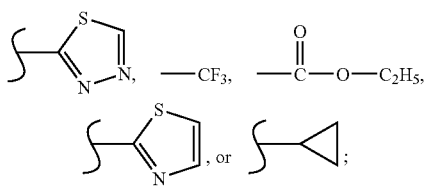

$R^x$ is H;
$R^y$ is H; and
$Z_a$ is a bond;
or a pharmaceutically acceptable salt thereof.

12. The compound as defined in claim 1 having the structure

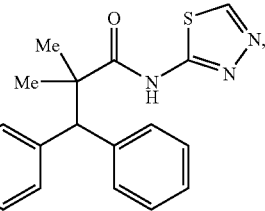

77
-continued
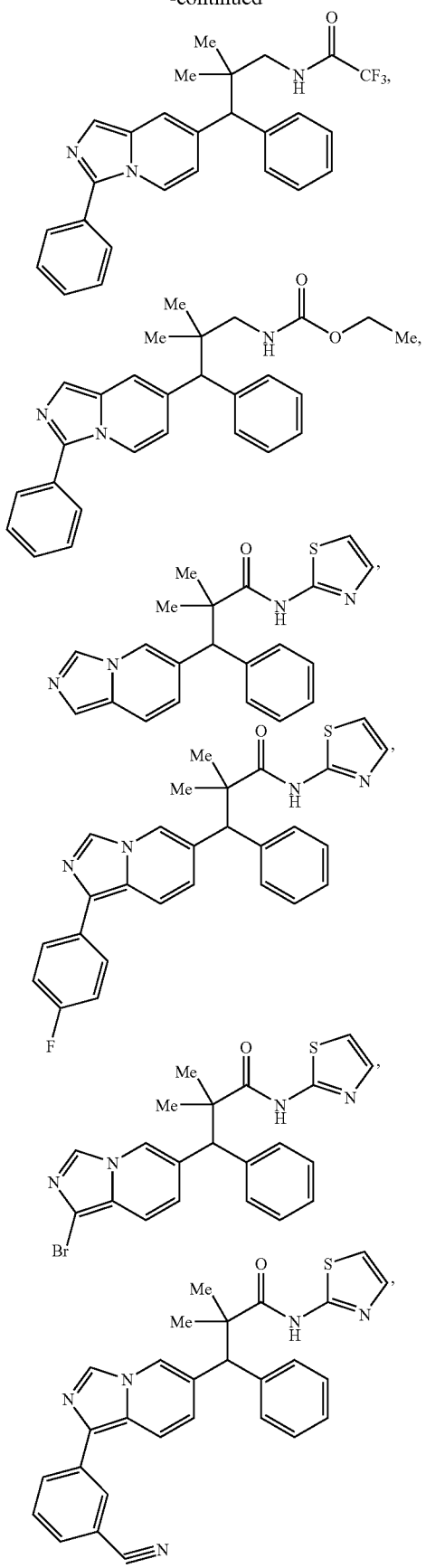
78
-continued
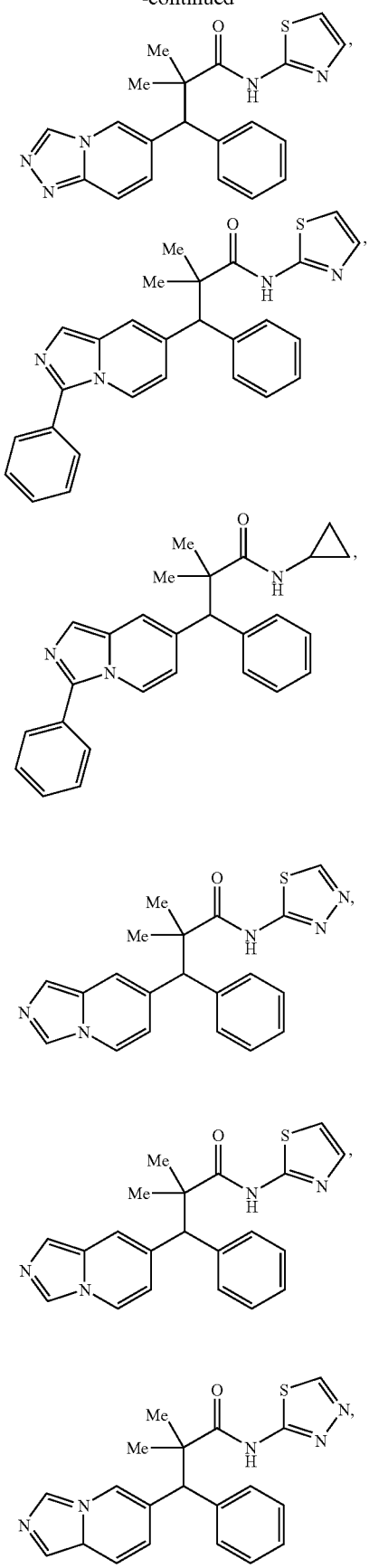

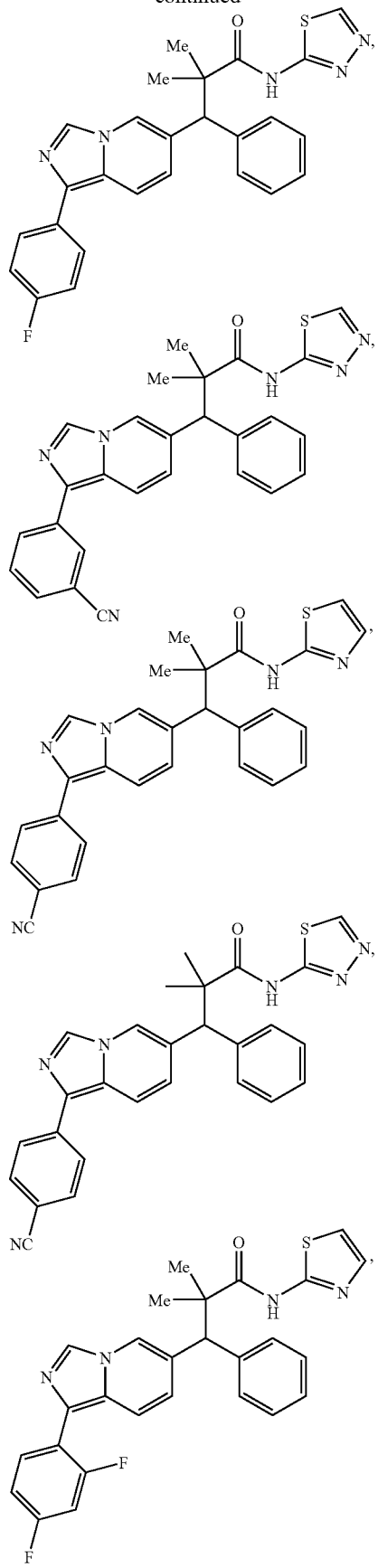
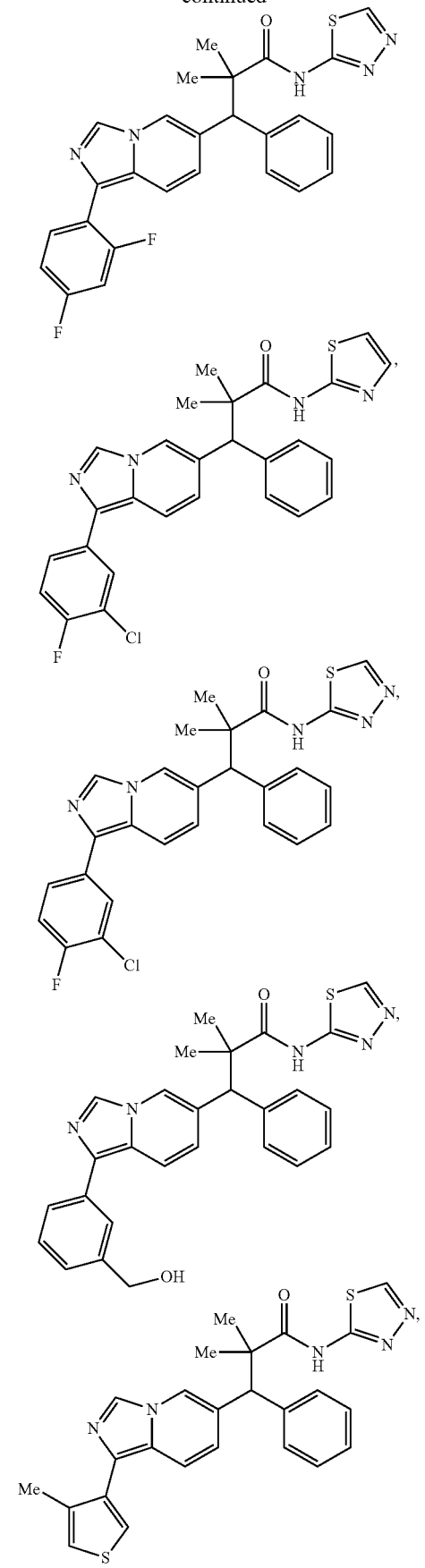

-continued

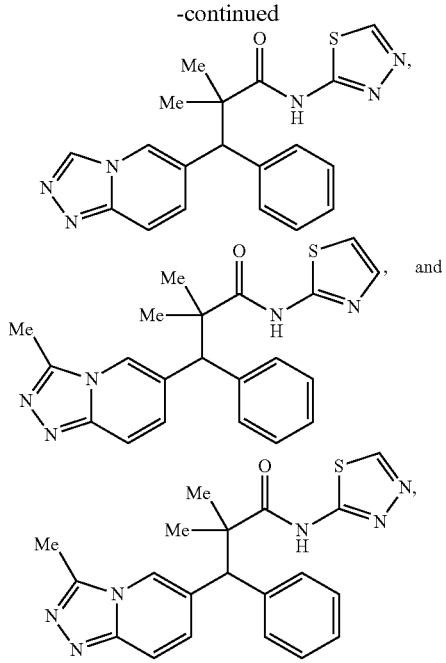

or a pharmaceutically acceptable salt thereof.

13. A pharmaceutical composition comprising a compound as defined in claim 1 and a pharmaceutically acceptable carrier therefor.

14. A pharmaceutical combination comprising a compound as defined in claim 1 and an antidiabetic agent, an anti-obesity agent, an antihypertensive agent, and/or an antiosteoporosis agent, wherein the antidiabetic agent is 1, 2, 3 or more of a metformin, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the antihypertensive agent is an ACE inhibitor, angiotensin II receptor antagonist, NEP/ACE inhibitor, calcium channel blocker and/or β-adrenergic blocker, and the antiosteoporosis agent is parathyroid hormone or a biphosphonate.

* * * * *

UNITED STATES PATENT AND TRADEMARK OFFICE
CERTIFICATE OF CORRECTION

PATENT NO. : 7,994,190 B2
APPLICATION NO. : 12/513228
DATED : August 9, 2011
INVENTOR(S) : T. G. Murali Dhar et al.

Page 1 of 1

It is certified that error appears in the above-identified patent and that said Letters Patent is hereby corrected as shown below:

In the Claims:

Claim 1:

Column 69, lines 46 to 53, change

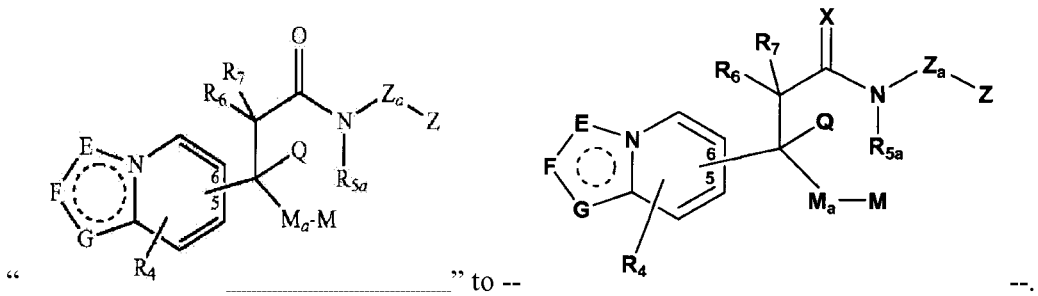

" to --                                                               --.

Claim 2:

Column 72, lines 23 to 30, change

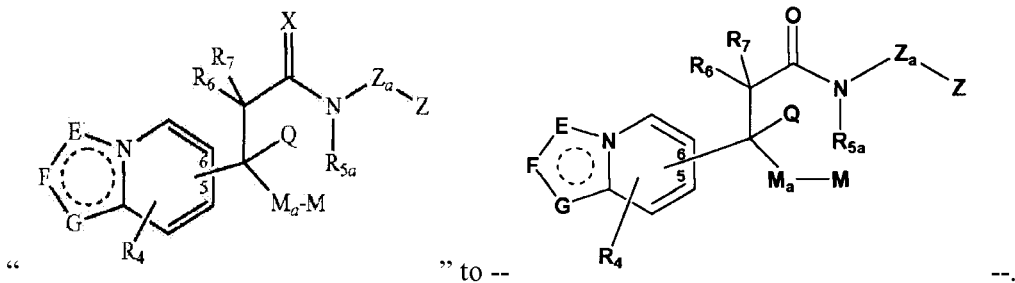

" to --                                                               --.

Claim 14:

Column 82, line 10, after "of", delete "a".

Signed and Sealed this
Twenty-ninth Day of November, 2011

David J. Kappos
*Director of the United States Patent and Trademark Office*